US011096947B2

(12) United States Patent
Tiedt et al.

(10) Patent No.: US 11,096,947 B2
(45) Date of Patent: Aug. 24, 2021

(54) COMBINATION PRODUCTS WITH TYROSINE KINASE INHIBITORS AND THEIR USE

(71) Applicant: Novartis AG, Basel (CH)

(72) Inventors: Ralph Tiedt, Basel (CH); Christian Chatenay-Rivauday, Saint Louis (FR); Moriko Ito, Basel (CH); Mikhail Akimov, Basel (CH); Bin Peng, Shanghai (CN); Ying Gong, Shanghai (CN)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/905,161

(22) Filed: Jun. 18, 2020

(65) Prior Publication Data

US 2020/0316081 A1    Oct. 8, 2020

Related U.S. Application Data

(63) Continuation of application No. 15/839,964, filed on Dec. 13, 2017, which is a continuation of application No. 14/388,334, filed as application No. PCT/CN2013/073678 on Apr. 3, 2013, now abandoned.

(60) Provisional application No. 61/619,490, filed on Apr. 3, 2012.

(51) Int. Cl.
| | |
|---|---|
| *C07D 491/04* | (2006.01) |
| *C07D 239/94* | (2006.01) |
| *C07D 487/04* | (2006.01) |
| *A61P 43/00* | (2006.01) |
| *A61P 35/00* | (2006.01) |
| *A61K 31/4709* | (2006.01) |
| *A61K 31/4706* | (2006.01) |
| *A61K 31/53* | (2006.01) |
| *A61K 31/517* | (2006.01) |
| *A61K 31/5025* | (2006.01) |
| *A61K 45/06* | (2006.01) |
| *A61K 31/5377* | (2006.01) |
| *A61K 31/498* | (2006.01) |

(52) U.S. Cl.
CPC ...... *A61K 31/5377* (2013.01); *A61K 31/4706* (2013.01); *A61K 31/4709* (2013.01); *A61K 31/498* (2013.01); *A61K 31/5025* (2013.01); *A61K 31/517* (2013.01); *A61K 31/53* (2013.01); *A61K 45/06* (2013.01); *C07D 239/94* (2013.01); *C07D 487/04* (2013.01); *C07D 491/04* (2013.01)

(58) Field of Classification Search
CPC .............. A61K 31/498; A61K 31/5377; A61K 31/4709; A61K 31/4706; A61K 31/53; A61K 31/517; A61K 31/5025; A61K 45/06; A61P 43/00; A61P 35/00; C07D 491/04; C07D 239/94; C07D 487/04
See application file for complete search history.

(56) References Cited

U.S. PATENT DOCUMENTS

| | | | |
|---|---|---|---|
| 7,767,675 | B2 | 8/2010 | Zhuo et al. |
| 8,263,631 | B2 | 9/2012 | Fujiwara et al. |
| 8,420,645 | B2 | 4/2013 | Weng et al. |
| 8,461,330 | B2 | 6/2013 | Zhuo et al. |
| 8,487,096 | B2 | 7/2013 | Zhuo et al. |
| 8,901,123 | B2 | 12/2014 | Weng et al. |
| 9,221,824 | B2 | 12/2015 | Zhuo et al. |
| 9,944,645 | B2 | 4/2018 | Zhuo et al. |
| 9,988,387 | B2 | 6/2018 | Zhuo et al. |
| 10,085,993 | B2 | 10/2018 | Goncalves et al. |
| 10,195,208 | B2 | 2/2019 | Hao et al. |
| 10,245,265 | B2 | 4/2019 | Weng et al. |
| 10,472,367 | B2 | 11/2019 | Zhuo et al. |
| 10,596,178 | B2 | 3/2020 | Goncalves et al. |
| 10,738,052 | B2 | 8/2020 | Zhuo et al. |
| 10,799,509 | B2 | 10/2020 | Weng et al. |
| 10,919,901 | B2 | 2/2021 | Zhuo et al. |
| 2007/0020261 | A1 | 1/2007 | Sliwkowski et al. |
| 2008/0166359 | A1 | 7/2008 | Lamb |
| 2011/0052581 | A1 | 3/2011 | Karlin et al. |
| 2011/0212967 | A1 | 9/2011 | Zhuo et al. |
| 2011/0229463 | A1 | 9/2011 | Pedersen et al. |
| 2012/0064090 | A1 | 3/2012 | Yano et al. |
| 2017/0209457 | A1 | 7/2017 | Hao et al. |
| 2017/0224692 | A1 | 8/2017 | Hao et al. |
| 2018/0098995 | A1* | 4/2018 | Tiedt ................. A61K 31/5025 |
| 2020/0253980 | A1 | 3/2020 | Caponigro et al. |

(Continued)

FOREIGN PATENT DOCUMENTS

| | | |
|---|---|---|
| KR | 10148970 B1 | 7/2014 |
| WO | 2007091422 A1 | 8/2007 |

(Continued)

OTHER PUBLICATIONS

Nissyoshi, Journal of Japanese Society of Gastroenterology, 2009, vol. 106, pp. 1712-1726, Abstract.
Igaku-No-Ayumi, Journal of Clinical and Experimental Medicine, Mar. 31, 2012, vol. 240, No. 13, pp. 1159-1164, Abstract.
Lack, et al_, "Targeting the Binding Function 3 (BF3) Site of the Human Androgen Recepto Through Virtual Screening", Journal of Medicinal Chemistry, vol. 54, No. 24, pp. 8563-8573, 2011.
Liu, et al., "A Novel Kinase Inhibitor, INCB28060, Bocks c-MET-Dependent Signaling, Neoplastic Activities, and Cross-Talk with EGFR and HER-3" Clinical Cancer Research; vol. 17 (22), pp. 7127-7138, 2011.

(Continued)

*Primary Examiner* — Sun Jae Yoo
(74) *Attorney, Agent, or Firm* — Elizabeth T. Karnas

(57) ABSTRACT

The present invention relates to pharmaceutical products comprising a combination of (i) a MET inhibitor and (ii) an EGFR inhibitor, or a pharmaceutically acceptable salt thereof, respectively, or a prodrug thereof, which are jointly active in the treatment of proliferative diseases, corresponding pharmaceutical formulations, uses, methods, processes, commercial packages and related invention embodiments.

11 Claims, 5 Drawing Sheets

(56) References Cited

U.S. PATENT DOCUMENTS

2020/0101077 A1 4/2020 Hao et al.
2020/0261573 A1 8/2020 Bilic et al.

FOREIGN PATENT DOCUMENTS

| WO | 2007091622 A1 | 8/2007 |
|---|---|---|
| WO | 2008064157 A1 | 5/2008 |
| WO | 2009143211 A2 | 11/2009 |
| WO | 2011018454 A1 | 2/2011 |
| WO | 2013184757 A1 | 12/2013 |
| WO | 2014113260 A1 | 7/2014 |
| WO | 2014122582 A1 | 8/2014 |

OTHER PUBLICATIONS

Stabile LP, et al., "Targeting of Both the c-Mel and EGFR Pathways Results in Additive Inhibition of Lung Tumorgenesis in Transgenic Mice", Cancers (Basel_2(4)), 2153-70 2110. Abstract, www.ncbi.nlm.nih.gov/pubmed/21390244.

Dulak AM, et al., HGF-independent Potentiation of EGFR action by c-Met Oncogene, 30 3625-35, 2011. Abstract: www.ncbi.nlm.nih.gov/pubmed/21423210.

Mashkovskiy, M.D., Medicinal Products: A manual for doctors, 14th edition, 2001, p. 11, vol. 1, S.B. Divov.

Kharkevich, D.A., Pharmacology Manual, Moscow: GEOTAR-Media, 10th edition, 2020, p. 73.

Kim, et al., "Targeting Colorectal Cancer with Human Anti-EGFR Monoclonocal Antibodies: Focus on Panitumumab", Biologies Targets & Therapy, 2008, vol. 2, No. 2, pp. 223-228.

Wadlow, et al., "Panitumumab in Patients with KRAS Wild-Type Colorectal Cancer after Progression on Cetuximab", The Oncologist, 2012, vol. 17, No. 14,2 pages.

Anonymous, "A Phase 1b, Open-label, Multicenter, Dose Escalation and Expansion Study, to Evaluate the Safety, Pharmacokinetics and Activity of INC280 in Combination with Cetuximab in c-MET Positive CRC and HNSCC Patients Who Have Progressed After Anti-EGFR Monoclonal Antibody Therapy", European Union Clinical Trials Register, Jun. 9, 2014, 6 pages, www.clinicaltrialsregister.eu/ctr-search/trial/2014-000579-20/ES [Retrieved on Feb. 13, 2018].

Harbinski, et al. "Rescue Screens with Secreted Proteins Reveal Compensatory Potential of Receptor Tyrosine Kinases in Driving Cancer Growth", Cancer Discovery, Oct. 2012, vol. 2, No. 10, pp. 948-959.

\* cited by examiner

COMBINATION PRODUCTS WITH TYROSINE KINASE INHIBITORS AND THEIR USE

RELATED APPLICATIONS

The present disclosure is a continuation of U.S. patent application Ser. No. 15/839,964 filed Dec. 13, 2017 which is a continuation of U.S. Ser. No. 14/388,334, filed Sep. 26, 2014, which is a National Stage Entry of PCT/CN2013/073678, filed Apr. 3, 2013, which claims priority to U.S. Provisional Application No. 61/619,490, filed Apr. 3, 2012, which is incorporated by reference herein in its entirety.

SUMMARY OF THE INVENTION

The present invention relates to pharmaceutical combinations, e.g. products, comprising a combination of (i) a MET inhibitor and (ii) an EGFR (ErbB-1) inhibitor, or a pharmaceutically acceptable salt thereof, respectively, or a prodrug thereof, which are jointly active in the treatment of proliferative diseases, corresponding pharmaceutical formulations, uses, methods, processes, commercial packages and related invention embodiments.

BACKGROUND OF THE INVENTION

Drugs that were designed to act against individual molecular targets often are not appropriate to combat diseases with more than one target as cause (multigenic diseases), such as cancer or other proliferative diseases.

In order to combat such diseases, one approach is to use single multi-target drugs—however, here it is required that the targets causally involved into manifestation of a disease are all hit by the drug considered. On the other hand, multi-target drugs may lead to undesired side effects as they may also have impact on targets not involved in the disease manifestation.

A different approach is to use a combination of drugs as multi-target drugs. In the best scenario, this may lead to a combined efficiency, e.g. synergy, thus even allowing a reduction of side effects caused by the single drugs when used alone.

Occasionally, the components (combination partners) of such drugs may impact separate targets to create a combination effect, and thus may create a combination effect going beyond what is achievable with the single compounds and/or when considering their isolated effects, respectively, either in the same pathway or separate pathways, within an individual cell or in separate cells in separate tissues. Alternatively, one component may alter the ability of another to reach its target, e.g. by inhibiting of efflux pumps or the like. Yet alternatively, the combination partners may bind to separate sites of the same target. These variants of target connectivity hamper the search for appropriate combinations by hugely increasing the possible types of interactions that might be useful for combination or not.

However, a desired cooperation, or even a synergy, using such drugs may not be found in many cases. As the number of pairwise (r=2) drug combinations increases according to the formula $n!/(r!(n-r)!)$ with the number of agents n being tested (e.g. testing 2000 agents would already generate 1,999,000 unique pairwise combinations), an appropriate screening method allowing high efficiency is necessary.

In addition, before any combination is considered, there is a crucial requirement to identify the pathways, enzymes, metabolic states or the like that are involved causally or in a supporting way in the disease manifestation.

In many cases, it is not even known at all that a given disease is multigenic.

Therefore, the search for appropriate combinations and amounts can properly be described to correspond to finding a needle in a haystack.

The proto-oncogen cMET (MET) encodes the protein Hepatocyte Growth Factor Receptor (HGFR) which has tyrosine kinase activity and is essential for embryonic development and wound healing. Upon Hepatocyte Growth Factor (HGF) stimulation, MET induces several biological responses, leading to invasive growth. Abnormal MET activation triggers tumor growth, formation of new blood vessels (angiogenesis) and metastasis, in various types of malignancies, including cancers of the kidney, liver, stomach, breast and brain. A number of MET kinase inhibitors are known, and alternatively inhibitors of HGF-induced MET (=HGFR) activation. The biological functions of c-MET (or c-MET signaling pathway) in normal tissues and human malignancies such as cancer have been well documented (Christensen, J. G. et al., Cancer Lett. 2005, 225(1):1-26; Corso, S. et al., Trends in Mol. Med. 2005, 11(6):284-292).

A dysregulated c-Met (c-MET) pathway plays important and sometimes causative (in the case of genetic alterations) roles in tumor formation, growth, maintenance and progression (Birchmeier, C. et al., Nat. Rev. Mol. Cell. Biol. 2003, 4(12):915-925; Boccaccio, C. et al., Nat. Rev. Cancer 2006, 6(8):637-645; Christensen, J. G. et al., Cancer Lett. 2005, 225(1):1-26). HGF and/or c-Met are overexpressed in significant portions of most human cancers, and are often associated with poor clinical outcomes such as more aggressive disease, disease progression, tumor metastasis and shortened patient survival. Further, patients with high levels of HGF/c-Met proteins are more resistance to chemotherapy and radiotherapy. In addition to the abnormal HGF/c-Met expression, c-Met receptor can also be activated in cancer patients through genetic mutations (both germline and somatic) and gene amplification. Although gene amplification and mutations are the most common genetic alterations that have been reported in patients, the receptor can also be activated by deletions, truncations, gene rearrangement.

The various cancers in which c-MET is implicated include, but are not limited to: carcinomas (e.g., bladder, breast, cervical, cholangiocarcinoma, colorectal, esophageal, gastric, head and neck, kidney, liver, lung, nasopharyngeal, ovarian, pancreas, prostate, thyroid); musculoskeletal sarcomas (e.g., osteosarcaoma, synovial sarcoma, rhabdomyosarcoma); soft tissue sarcomas (e.g., MFH/fibrosarcoma, leiomyosarcoma, Kaposi's sarcoma); hematopoietic malignancies (e.g., multiple myeloma, lymphomas, adult T cell leukemia, acute myelogenous leukemia, chronic myeloid leukemia); and other neoplasms (e.g., glioblastomas, astrocytomas, melanoma, mesothelioma and Wilm's tumor (www.vai.org/met/; Christensen, J. G. et al., Cancer Lett. 2005, 225(1):1-26).

The notion that the activated c-MET pathway contributes to tumor formation and progression and could be a good target for effective cancer intervention has been further solidified by numerous preclinical studies (Birchmeier, C. et al., Nat. Rev. Mol. Cell Biol. 2003, 4(12):915-925; Christensen, J. G. et al., Cancer Lett. 2005, 225(1):1-26; Corso, S. et al., Trends in Mol. Med. 2005, 11(6): 284-292). For example, studies showed that the tpr-met fusion gene, overexpression of c-met and activated c-met mutations (collectively referred to herein as MET) all caused oncogenic transformation of various model cell lines and resulted in tumor formation and metastasis in mice. More importantly, significant anti-tumor (sometimes tumor regression) and anti-metastasis activities have been demonstrated in vitro and in vivo with agents that specifically impair and/or block HGF/c-MET signaling. Those agents include anti-HGF and anti-c-Met antibodies, HGF peptide antagonists, decoy c-Met receptor, c-Met peptide antagonists, dominant negative c-Met mutations, c-Met specific antisense oligonucleotides and ribozymes, and selective small molecule c-Met kinase inhibitors (Christensen, J. G. et al., Cancer Lett. 2005, 225(1):1-26).

In addition to the established role in cancer, abnormal HGF/MET signaling is also implicated in atherosclerosis, lung fibrosis, renal fibrosis and regeneration, liver diseases, allergic disorders, inflammatory and autoimmune disorders, cerebrovascular diseases, cardiovascular diseases, conditions associated with organ transplantation (Ma, H. et al., Atherosclerosis. 2002, 164(1):79-87; Crestani, B. et al., Lab. Invest. 2002, 82(8):1015-1022; Sequra-Flores, A. A. et al., Rev. Gastroenterol. Mex. 2004, 69(4)243-250; Morishita, R. et al., Curr. Gene Ther. 2004, 4(2)199-206; Morishita, R. et al., Endocr. J. 2002, 49(3)273-284; Liu, Y., Curr. Opin. Nephrol. Hypertens. 2002, 11(1):23-30; Matsumoto, K. et al., Kidney Int. 2001, 59(6):2023-2038; Balkovetz, D. F. et al., Int. Rev. Cytol. 1999, 186:225-250; Miyazawa, T. et al., J. Cereb. Blood Flow Metab. 1998, 18(4)345-348; Koch, A. E. et al., Arthritis Rheum. 1996, 39(9):1566-1575; Futamatsu, H. et al., Circ. Res. 2005, 96(8)823-830; Eguchi, S. et al., Clin. Transplant. 1999, 13(6)536-544).

The Epidermal Growth Factor Receptor (EGFR, aka ErbB-1; HER1 in humans), is a receptor for ligands of the epidermal growth factor family. Several types of cancers are known to be dependent on EGFR over-activity or over-expression, such as lung cancer, anal cancers, glioblastoma multiforme and many other mainly epithelial cancers.

Cancer is often dependent on the genetic alteration of receptor tyrosine kinases (RTKs) e.g. by point mutation, gene amplification or chromosomal translocation which leads to uncontrolled activity of these RTKs which thus become oncogenic. Cell proliferation of cancer cells is dependent on the activity of these aberrant RTKs.

When treating the resulting proliferative diseases, often inhibitors of the oncogene RTK involved are used. However, often, after a certain time of treatment, resistance to the drug used is observed. One mechanism of resistance can involve the target RTK, compromising binding or activity of the therapeutic agent. Another mechanism is compensatory activation of an alternative kinase that continues to drive cancer growth when the primary kinase is inhibited. A well-characterized example covering both types of mechanisms is acquired resistance to the epidermal growth factor receptor (EGFR) gefitinib and erlotinib in non-small cancer (NSCLC) carrying activating EGFR mutations (see Lynch, T. J., et al., N Engl J Med, 350: 2129-2139, 2004; or Paez, J. G., et al., Science, 304: 1497-1500, 2004). For example, MET activation can compensate for loss of EGFR activity (by inhibition) by downstream activation of signal molecules such as HER3, such as MET amplification may compensate, or its ligand hepatocyte growth factor may activate MET (see Engelman, J. A., et al., Science, 316: 1039-1043, 2007; Yano, S., et al., Cancer Res, 68: 9479-9487, 2008; and Turke, A. B., et al., Cancer Cell, 17: 77-88, 2010). It is also known that MET-dependent cancer cell lines (the proliferation of which depends on the activity of MET) can be rescued from MET inhibitors by ligand-induced EGFR activation (see Bachleitner-Hofmann, T., et al., Mol Cancer Ther, 7: 3499-3508, 2008).

General Description of the Invention

Using cancer cells originally dependent on MET and/or EGFR (that is, their activity), a by-pass of dependence through ligand-mediated activation of alternative receptor tyrosine kinases (RTKs) was observed. By-pass mechanisms were discovered when treating MET- or FGFR-dependent lines with a corresponding selective inhibitor (that is, MET-dependent lines with a MET inhibitor and FGFR-dependent lines with an FGFR inhibitor) and at the same time adding supernatants from cells transfected with cDNA coding for various secreted proteins It could be shown that the MET and FGFR RTKs can compensate for loss of each other, thus leading to "rescue" of proliferating cells if only one of these RTKs is inhibited by an appropriate drug.

It was surprisingly found that combined inhibition of these RTKs can lead to synergistic anti-cancer activity especially when MET and an FGFR RTK are both active and then, according to the invention, can be inhibited simultaneously or jointly sequentially.

Specific Description of the Invention

The present invention, according to a first embodiment, relates to a pharmaceutical combination (e.g. combination product) comprising (i) a MET inhibitor and (ii) an EGFR inhibitor, or a pharmaceutically acceptable salt thereof, respectively, or a prodrug thereof, respectively, and at least one pharmaceutically acceptable carrier.

A further embodiment of this invention provides a combination (e.g. combination product) comprising a quantity which is jointly therapeutically effective against an EGFR tyrosine kinase activity and/or MET tyrosine kinase activity mediated disease, especially a cancer, comprising the combination partners (i) EGFR tyrosine kinase inhibitor and (ii) MET tyrosine kinase inhibitor, or, respectively, a pharmaceutically acceptable salt thereof, and at least one pharmaceutically acceptable carrier material.

A further embodiment relates to the use of the inventive combination (e.g. combination product) for treating an EGFR tyrosine kinase activity and/or MET tyrosine kinase activity mediated disease, especially a cancer.

A further embodiment relates to the use of a combination of (i) an EGFR tyrosine kinase inhibitor and (ii) a MET tyrosine kinase inhibitor or, respectively, a pharmaceutically acceptable salt thereof, for the manufacture of a medicament or a pharmaceutical product for treating an EGFR tyrosine kinase activity and/or MET tyrosine kinase activity mediated disease, especially a cancer.

A further embodiment relates to a method of treating an EGFR tyrosine kinase activity and/or MET tyrosine kinase activity mediated disease, especially a cancer, with a combination of (i) an EGFR tyrosine kinase inhibitor and (ii) a MET tyrosine kinase inhibitor or, respectively, a pharmaceutically acceptable salt thereof.

A further embodiment relates to a method for the treatment of an EGFR tyrosine kinase activity and/or MET tyrosine kinase activity mediated disease, especially a cancer, said method comprising administering an effective amount of a combi-nation of or a combination product comprising (i) an EGFR tyrosine kinase inhibitor and (ii) a MET tyrosine kinase inhibitor to a subject in need thereof, such as a warm-blooded animal, in particular a human.

Yet a further embodiment of present invention relates to a pharmaceutical product or a commercial package comprising a combination product according to the invention described herein, in particular together with instructions for simultaneous, separate or sequential use (especially for being jointly active) thereof in the treatment of an EGFR tyrosine kinase activity and/or MET tyrosine kinase activity mediated disease, especially a cancer, in particular for use in the treatment of an EGFR tyrosine kinase activity and/or MET tyrosine kinase activity mediated disease, especially a cancer.

A further embodiment of present invention relates to the use of (i) an EGFR tyrosine kinase inhibitor and (ii) a MET tyrosine kinase inhibitor or, respectively, a pharmaceutically acceptable salt thereof, for the preparation of a combination (e.g. a combination product) according to present invention.

The following definitions show more specific embodiments of general features or expressions which can be used to replace one, more than one or all general features or expressions in the invention embodiments described hereinbefore and hereinafter, thus leading to more specific invention embodiments.

Among the MET tyrosine kinase inhibitors useful according to the invention, those disclosed in WO 2011/018454 (incorporated herein by reference especially with regard to the classes of compounds and compounds disclosed therein) are a particular embodiment, especially those of the formula (I), (I)

wherein
Y is C or N;
X is CH or N;
B is CH or N;
A is a ring;
such that when X is CH and B is N, ring A is ring Ai or ring Aii;

Ai

Aii when X is N and B is N, ring A is Aiii;

Aiii and when X is N and B is N, or X is N and B is CH, ring A is Ai;

Ai $R^1$ is a group selected from i, ii and iii:

i ii iii wherein $R^5$ is heteroaryl;
$R^6$ is hydrogen, deuterium, OH, methyl or halo;
$R^7$ is hydrogen, deuterium, halo, or $(C_1\text{-}C_3)$alkyl, wherein said $(C_1\text{-}C_3)$alkyl is optionally substituted by one or more substituents independently selected from OH and halo;
or $R^6$ and $R^7$, together with the carbon to which they are attached form cyclopropyl, wherein said cyclopropyl is optionally substituted by methyl;
n is 0, 1 or 2;
$R^2$ is hydrogen, $NH_2$, or $(C_1\text{-}C_4)$alkyl, wherein said $(C_1\text{-}C_4)$alkyl is optionally substituted by one or more substituents independently selected from OH, $NH_2$ and halo;
$R^3$ is hydrogen, —$CONH_2$, —$CONH(C_1\text{-}C_4)$alkyl, —CONHphenyl, wherein the phenyl of said CONHphenyl is optionally substituted by one or more halo, —$(C_1\text{-}C_4)$alkyl, —$CO(C_1\text{-}C_4)$alkyl, —$CO_2(C_1\text{-}C_4)$alkyl, phenyl, heteroaryl, —COheteroaryl, —$CSNH_2$, —$CSNH(C_1\text{-}C_4)$alkyl, —CSNHbenzyl, —$SO_2(C_1\text{-}C_4)$alkyl or —$COCH_2$heterocyclyl, said heterocyclyl being optionally substituted by $(C_1\text{-}C_3)$alkyl;
$R^4$ is hydrogen or $(C_1\text{-}C_3)$alkyl;
or $R^3$ and $R^4$ together with the nitrogen to which they are attached form a 5 or 6 membered saturated or partially unsaturated monocyclic group comprising 1 ring N atom to which $R^3$ and $R^4$ are attached and optionally 1 additional ring heteroatom independently selected from N, O and S, wherein said monocyclic group is substituted by one or two =O substituents;
or a pharmaceutically acceptable salt thereof.

Especially preferred of the group of compounds of the formula I which are MET tyrosine kinase inhibitors is that with the name (E)-2-(1-(3-((7-fluoroquinolin-6-yl)methyl)imidazo[1,2-b]pyridazin-6-yl)ethylidene)hydrazinecarboxamide (also called Cpd. A in the following) which has the formula:

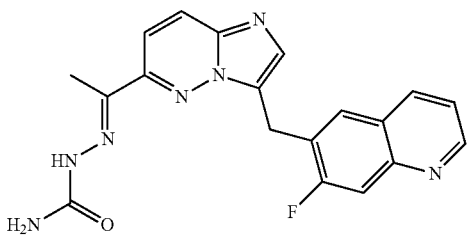 [SMILES: C/C(=N\NC(N)=O)c1ccc2ncc(Cc3cc4cccnc4cc3F)n2n1]

See WO 11 018454, Example 1.

Among the MET tyrosine kinase inhibitors useful according to the invention, as a particular embodiment there are also to be mentioned those disclosed, together with methods for their manufacture, in WO 2008/064157 (incorporated herein by reference especially with regard to the disclosed compounds and compound classes), especially the compounds having Formula III:

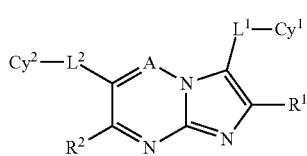

or pharmaceutically acceptable salts thereof or prodrugs thereof, wherein:

A is N or $CR^3$;

$Cy^1$ is aryl, heteroaryl, cycloalkyl, or heterocycloalkyl, each optionally substituted by 1, 2, 3, 4, or 5 —W—X—Y—Z;

$Cy^2$ is aryl, heteroaryl, cycloalkyl, or heterocycloalkyl, each optionally substituted by 1, 2, 3, 4, or 5 —W'—X'—Y'—Z';

$L^1$ is $(CR^4R^5)_m$, $(CR^4R^5)_p$-(cycloalkylene)-$(CR^4R^5)_q$, $(CR^4R^5)_p$-(arylene)-$(CR^4R^5)_q$, $(CR^4R^5)_p$(heterocycloalkylene)-$(CR^4R^5)_q$, $(CR^4R^5)_p$-(heteroarylene)-$(CR^4R^5)_q$, $(CR^4R^5)_pO(CR^4R^5)_q$, $(CR^4R^5)_pS(CR^4R^5)_q$, $(CR^4R^5)_pC(O)(CR^4R^5)_q$, $(CR^4R^5)_pC(O)NR^6(CR^4R^5)_q$, $(CR^4R^5)_pC(O)O(CR^4R^5)_q$, $(CR^4R^5)_pOC(O)(CR^4R^5)_q$, $(CR^4R^5)_pOC(O)NR^6(CR^4R^5)_q$, $(CR^4R^5)_pNR^6(CR^4R^5)_q$, $(CR^4R^5)_pNR^6C(O)NR^6(CR^4R^5)_q$, $(CR^4R^5)_pS(O)(CR^4R^5)_q$, $(CR^4R^5)_pS(O)NR^6(CR^4R^5)_q$, $(CR^4R^5)_pS(O)_2(CR^4R^5)_q$, or $(CR^4R^5)_pS(O)_2NR^6(CR^4R^5)_q$, wherein said cycloalkylene, arylene, heterocycloalkylene, or heteroarylene is optionally substituted with 1, 2, or 3 substituents independently selected from $Cy^3$, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)NR^cR^d$, $NR^cC(O)OR^a$, $C(=NR^g)NR^cR^d$, $NR^cC(=NR^g)NR^cR^d$, $P(R^f)_2$, $P(OR^e)_2$, $P(O)R^eR^f$, $P(O)OR^eOR^f$, $S(O)R^b$, $S(O)NR^cR^d$, $S(O)_2R^b$, $NR^cS(O)_2R^b$, and $S(O)_2NR^cR^d$;

$L^2$ is $(CR^7R^8)_r$, $(CR^7R^8)_s$-(cycloalkylene)-$(CR^7R^8)_t$, $(CR^7R^8)_s$-(arylene)-$(CR^7R^8)_t$, $(CR^7R^8)_s$-(heterocycloalkylene)-$(CR^7R^8)_t$, $(CR^7R^8)_s$-(heteroarylene)-$(CR^7R^8)_t$, $(CR^7R^8)_sO(CR^7R^8)_t$, $(CR^7R^8)_sS(CR^7R^8)_t$, $(CR^7R^8)_sC(O)(CR^7R^8)_t$, $(CR^7R^8)_sC(O)NR^9(CR^7R^8)_t$, $(CR^7R^8)_sC(O)O(CR^7R^8)_t$, $(CR^7R^8)_sOC(O)(CR^7R^8)_t$, $(CR^7R^8)_sOC(O)NR^9(CR^7R^8)_t$, $(CR^7R^8)_sNR^9(CR^7R^8)_t$, $(CR^7R^8)_sNR^9C(O)NR^9(CR^7R^8)_t$, $(CR^7R^8)_sS(O)(CR^7R^8)_t$, $(CR^7R^8)_sS(O)NR^7(CR^8R^9)_t$, $(CR^7R^8)_sS(O)_2(CR^7R^8)_t$, or $(CR^7R^8)_sS(O)_2NR^9(CR^7R^8)_t$, wherein said cycloalkylene, arylene, heterocycloalkylene, or heteroarylene is optionally substituted with 1, 2, or 3 substituents independently selected from $Cy^4$, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{d1}$, $NR^{c1}C(O)NR^{c1}R^{d1}$, $NR^{c1}C(O)OR^{a1}$, $C(=NR^g)NR^{c1}R^{d1}$, $NR^{c1}C(=NR^g)NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

$R^1$ is H or —W"—X"—Y"—Z";

$R^2$ is H, halo, $C_{1-6}$ alkyl, $C_{2-6}$ alkenyl, $C_{2-6}$ alkynyl, $C_{1-6}$ haloalkyl, CN, $NO_2$, $OR^A$, $SR^A$, $C(O)R^B$, $C(O)NR^CR^D$, $C(O)OR^A$, $OC(O)R^B$, $OC(O)NR^CR^D$, $NR^CR^D$, $NR^CC(O)R^B$, $NR^CC(O)NR^CR^D$, $NR^CC(O)OR^A$, $S(O)R^B$, $S(O)NR^CR^D$, $S(O)_2R^B$, $NR^CS(O)_2R^B$, or $S(O)_2NR^CR^D$;

$R^3$ is H, cycloalkyl, aryl, heterocycloalkyl, heteroaryl, halo, $C_{1-6}$ alkyl, $C_{2-6}$ alkenyl, $C_{2-6}$ alkynyl, $C_{1-6}$ haloalkyl, CN, $NO_2$, $OR^A$, $SR^A$, $(O)R^B$, $C(O)NR^CR^D$, $C(O)OR^A$, $OC(O)R^B$, $OC(O)NR^CR^D$, $NR^CR^D$, $NR^CC(O)R^B$, $NR^CC(O)NR^CR^D$, $NR^CC(O)OR^A$, $S(O)R^B$, $S(O)NR^CR^D$, $S(O)_2R^B$, $NR^CS(O)_2R^B$, and $S(O)_2NR^CR^D$; wherein said cycloalkyl, aryl, heterocycloalkyl, heteroaryl, or $C_{1-6}$ alkyl is optionally substituted with 1, 2, or 3 substituents independently selected from $Cy^5$, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a1}$, $SR^{a1}$, $C(O)R^{d1}$, $C(O)NR^{c1}R^{d1}$, $C(O)OR^{a1}$, $OC(O)R^{a1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $C(=NR^9)NR^{c1}R^{d1}$, $NR^{c1}C(=NR^9)NR^{c1}R^{d1}$, $P(R^{f1})_2$, $P(OR^{e1})_2$, $P(O)R^{e1}R^{f1}$, $P(O)OR^{e1}OR^{f1}$, $S(O)R^{b1}$, $S(O)NR^{c1}R^{d1}$, $S(O)_2R^{b1}$, $NR^{c1}S(O)_2R^{b1}$, and $S(O)_2NR^{c1}R^{d1}$;

or $R^2$ and -$L^2$-$Cy^2$ are linked together to form a group of formula:

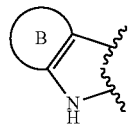

wherein ring B is a fused aryl or fused heteroaryl ring, each optionally substituted with 1, 2, or 3 —W'—X'—Y'—Z';

$R^4$ and $R^5$ are independently selected from H, halo, OH, $C_{1-6}$ alkyl, $C_{2-6}$ alkenyl, $C_{2-6}$ alkynyl, $C_{1-6}$ alkoxy, alkoxyalkyl, cyanoalkyl, heterocycloalkyl, cycloalkyl, $C_{1-6}$ haloalkyl, CN, and $NO_2$;

or $R^4$ and $R^5$ together with the C atom to which they are attached form a 3, 4, 5, 6, or 7-membered cycloalkyl or heterocycloalkyl ring, each optionally substituted by 1, 2, or 3 substituents independently selected from halo, OH, $C_{1-6}$ alkyl, $C_{2-6}$ alkenyl, $C_{2-6}$ alkynyl, $C_{1-6}$ alkoxy, alkoxyalkyl, cyanoalkyl, heterocycloalkyl, cycloalkyl, $C_{1-6}$ haloalkyl, CN, and $NO_2$;

$R^6$ is H, $C_{1-6}$ alkyl, $C_{2-6}$ alkenyl, or $C_{2-6}$ alkynyl;

$R^7$ and $R^8$ are independently selected from H, halo, OH, $C_{1-6}$ alkyl, $C_{2-6}$ alkenyl, $C_{2-6}$ alkynyl, $C_{1-6}$ alkoxy, $C_{1-6}$ haloalkyl, CN, and $NO_2$;

or $R^7$ and $R^8$ together with the C atom to which they are attached form a 3, 4, 5, 6, or 7-membered cycloalkyl or heterocycloalkyl ring, each optionally substituted by 1, 2, or 3 substituent independently selected from halo, OH, $C_{1-6}$ alkyl, $C_{2-6}$ alkenyl, $C_{2-6}$ alkynyl, $C_{1-6}$ alkoxy, $C_{1-6}$ haloalkyl, CN, and $NO_2$;

$R^9$ is H, $C_{1-6}$ alkyl, $C_{2-6}$ alkenyl, or $C_{2-6}$ alkynyl;

W, W', and W" are independently absent or independently selected from $C_{1-6}$ alkylene, $C_{2-6}$ alkenylene, $C_{2-6}$ alkynylene, O, S, $NR^h$, CO, COO, $CONR^h$, SO, $SO_2$, $SONR^h$ and $NR^hCONR^i$, wherein each of the $C_{1-6}$ alkylene, $C_{2-6}$ alkenylene, and $C_{2-6}$ alkynylene is optionally substituted by 1, 2 or 3 substituents independently selected from halo, $C_{1-6}$ alkyl, $C_{1-6}$ haloalkyl, OH, $C_{1-6}$ alkoxy, $C_{1-6}$ haloalkoxy, amino, $C_{1-6}$ alkylamino, and $C_{2-8}$ dialkylamino;

X, X', and X" are independently absent or independently selected from $C_{1-6}$ alkylene, $C_{2-6}$ alkenylene, $C_{2-6}$ alkynylene, arylene, cycloalkylene, heteroarylene, and heterocycloalkylene, wherein each of the $C_{1-6}$ alkylene, $C_{2-6}$ alkenylene, $C_{2-6}$ alkynylene, arylene, cycloalkylene, heteroarylene, and heterocycloalkylene is optionally substituted by 1, 2 or 3 substituents independently selected from halo, CN, $NO_2$, OH, $C_{1-6}$ alkyl, $C_{1-6}$ haloalkyl, $C_{2-8}$ alkoxyalkyl, $C_{1-6}$ alkoxy, $C_{1-6}$ haloalkoxy, $C_{2-8}$ alkoxyalkoxy, cycloalkyl, heterocycloalkyl, $C(O)OR^j$, $C(O)NR^hR^i$, amino, $C_{1-6}$ alkylamino, and $C_{2-8}$ dialkylamino;

Y, Y', and Y" are independently absent or independently selected from $C_{1-6}$ alkylene, $C_{2-6}$ alkenylene, $C_{2-6}$ alkynylene, O, S, $NR^h$, CO, COO, $CONR^h$, SO, $SO_2$, $SONR^h$, and $NR^hCONR^i$, wherein each of the $C_{1-6}$ alkylene, $C_{2-6}$ alkenylene, and $C_{2-6}$ alkynylene is optionally substituted by 1, 2 or 3 substituents independently selected from halo, $C_{1-6}$ alkyl, $C_{1-6}$ haloalkyl, OH, $C_{1-6}$ alkoxy, $C_{1-6}$ haloalkoxy, amino, $C_{1-6}$ alkylamino, and $C_{2-8}$ dialkylamino;

Z, Z', and Z" are independently selected from H, halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^2C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^{c2}S(O)_2R^{b2}$, $S(O)_2NR^{c2}R^{d2}$, aryl, cycloalkyl, heteroaryl, and heterocycloalkyl, wherein said $C_{1-6}$ alkyl, $C_{2-6}$ alkenyl, $C_{2-6}$ alkynyl, aryl, cycloalkyl, heteroaryl, and heterocycloalkyl are optionally substituted by 1, 2, 3, 4 or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $C(=NR^g)NR^{c2}R^{d2}$, $NR^{c2}C(=NR^g)NR^{c2}R^{d2}$, $P(R^{f2})_2$, $P(OR^{e2})_2$, $P(O)R^{e2}R^{f2}$, $P(O)OR^{e2}OR^{f2}$, $S(O)R^{b2}$, $S(O)NR^{c2}R^{d2}$, $S(O)_2R^{b2}$, $NR^2S(O)_2R^{b2}$, and $S(O)_2NR^{c2}R^{d2}$;

wherein two adjacent —W—X—Y—Z, together with the atoms to which they are attached, optionally form a fused 4-20 membered cycloalkyl ring or a fused 4-20 membered heterocycloalkyl ring, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^g)NR^{c3}R^{d3}$, $NR^{c3}C(=NR^g)NR^{c3}R^{d3}$, $S(O)R^{b3}$, $S(O)NR^{c3}R^{d3}$, $S(O)_2R^{b3}$, $NR^{c3}S(O)_2R^{b3}$, $S(O)_2NR^{c3}R^{d3}$, aryl, cycloalkyl, heteroaryl, and heterocycloalkyl;

wherein two adjacent —W'—X'—Y'—Z', together with the atoms to which they are attached, optionally form a fused 4-20 membered cycloalkyl ring or a fused 4-20 membered heterocycloalkyl ring, each optionally substituted by 1, 2, or 3 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^g)NR^{c3}R^{d3}$, $NR^{c3}C(=NR^g)NR^{c3}R^{d3}$, $S(O)R^{b3}$, $S(O)NR^{c3}R^{d3}$, $S(O)_2R^{b3}$, $NR^3S(O)_2R^{b3}$, $S(O)_2NR^{c3}R^{d3}$, aryl, cycloalkyl, heteroaryl, and heterocycloalkyl;

$Cy^3$, $Cy^4$, and $Cy^5$ are independently selected from aryl, cycloalkyl, heteroaryl, and heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $N_3$, $OR^{a4}$, $SR^{a4}$, $C(O)R^{b4}$, $C(O)NR^{c4}R^{d4}$, $C(O)OR^{a4}$, $C(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^g)NR^{c4}R^{d4}$, $NR^{c4}C(=NR^g)NR^{c4}R^{d4}$, $P(R^{f4})_2$, $P(OR^4)_2$, $P(O)R^{e4}R^{f4}$, $P(O)OR^{e4}OR^{f4}$, $S(O)R^{b4}$, $S(O)NR^{c4}R^{d4}$, $S(O)_2R^{b4}$, $NR^{c4}S(O)_2R^{b4}$, and $S(O)_2NR^{c4}R^{d4}$;

$R^A$ is H, $C_{1-4}$ alkyl, $C_{2-4}$ alkenyl, $C_{2-4}$ alkynyl, cycloalkyl, heterocycloalkyl, aryl, or heteroaryl wherein said $C_{1-4}$ alkyl, $C_{2-4}$ alkenyl, $C_{2-4}$ alkynyl, cycloalkyl, heterocycloalkyl, aryl or heteroaryl is optionally substituted with 1, 2, or 3 substituents independently selected from OH, CN, amino, halo, and $C_{1-4}$ alkyl;

$R^B$ is H, $C_{1-4}$ alkyl, $C_{2-4}$ alkenyl, $C_{2-4}$ alkynyl, cycloalkyl, heterocycloalkyl, aryl, or heteroaryl wherein said $C_{1-4}$ alkyl, $C_{2-4}$ alkenyl, or $C_{2-4}$ alkynyl, cycloalkyl, heterocycloalkyl, aryl, or heteroaryl is optionally substituted with 1, 2, or 3 substituents independently selected from OH, CN, amino, halo, and $C_{1-4}$ alkyl;

$R^C$ and $R^D$ are independently selected from H, $C_{1-4}$ alkyl, $C_{2-4}$ alkenyl, or $C_{2-4}$ alkynyl, wherein said $C_{1-4}$ alkyl, $C_{2-4}$ alkenyl, or $C_{2-4}$ alkynyl, is optionally substituted with 1, 2, or 3 substituents independently selected from OH, CN, amino, halo, and $C_{1-4}$ alkyl;

or $R^C$ and $R^D$ together with the N atom to which they are attached form a 4-, 5-, 6- or 7-membered heterocloalkyl group or heteroaryl group, each optionally substituted with 1, 2, or 3 substituents independently selected from OH, CN, amino, halo, and $C_{1-4}$ alkyl;

$R^a$, $R^{a1}$, $R^{a2}$, $R^{a3}$, and $R^{a4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^b$, $R^{b1}$, $R^{b2}$, $R^{b3}$, and $R^{b4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^c$ and $R^d$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^c$ and $R^d$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c1}$ and $R^{d1}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c1}$ and $R^{d1}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c2}$ and $R^{d2}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl, heterocycloalkylalkyl, arylcycloalkyl, arylheterocycloalkyl, arylheteroaryl, biaryl, heteroarylcycloalkyl, heteroarylheterocycloalkyl, heteroarylaryl, and biheteroaryl are each optionally substituted with 1, 2, or 3 substituents independently selected from OH, CN, amino, halo, $C_{1-6}$ alkyl, $C_{1-6}$ alkoxy, $C_{1-6}$ haloalkyl, $C_{1-6}$ haloalkoxy, hydroxyalkyl, cyanoalkyl, aryl, heteroaryl, $C(O)OR^{a4}$, $C(O)R^{b4}$, $S(O)_2R^{b3}$, alkoxyalkyl, and alkoxyalkoxy;

or $R^{c2}$ and $R^{d2}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, $C_{1-6}$ haloalkoxy, hydroxyalkyl, cyanoalkyl, aryl, heteroaryl, $C(O)OR^{a4}$, $C(O)R^{b4}$, $S(O)_2 R^{b3}$, alkoxyalkyl, and alkoxyalkoxy;

$R^{c3}$ and $R^{d3}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c3}$ and $R^{d3}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^{c4}$ and $R^{d4}$ are independently selected from H, $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl, wherein said $C_{1-10}$ alkyl, $C_{1-6}$ haloalkyl, $C_{2-6}$ alkenyl, $C_{2-6}$ alkynyl, aryl, heteroaryl, cycloalkyl, heterocycloalkyl, arylalkyl, heteroarylalkyl, cycloalkylalkyl or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c4}$ and $R^{d4}$ together with the N atom to which they are attached form a 4-, 5-, 6- or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

$R^e$, $R^{e1}$, $R^{e2}$, and $R^{e4}$ are independently selected from H, $C_{1-6}$ alkyl, $C_{1-6}$ haloalkyl, $C_{2-6}$ alkenyl, $(C_{1-6}$ alkoxy)-$C_{1-6}$ alkyl, $C_{2-6}$ alkynyl, aryl, cycloalkyl, heteroaryl, heterocycloalkyl, arylalkyl, cycloalkylalkyl, heteroarylalkyl, and heterocycloalkylalkyl;

$R^f$, $R^{f1}$, $R^{f2}$, and $R^{f4}$ are independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, and heterocycloalkyl;

$R^g$ is H, CN, and $NO_2$;

$R^h$ and $R^i$ are independently selected from H and $C_{1-6}$ alkyl;

$R^j$ is H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl;

m is 0, 1, 2, 3, 4, 5, or 6;

p is 0, 1, 2, 3, or 4;

q is 0, 1, 2, 3, or 4;

r is 0, 1, 2, 3, 4, 5, or 6;

s is 0, 1, 2, 3, or 4; and t is 0, 1, 2, 3, or 4.

In some embodiments, the compounds of formula III useful according to the invention have Formula IIIA:

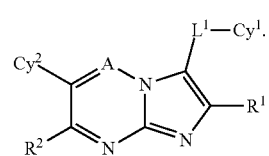

IIIA

In some embodiments, the compounds of formula III useful according to the invention have Formula IIIB:

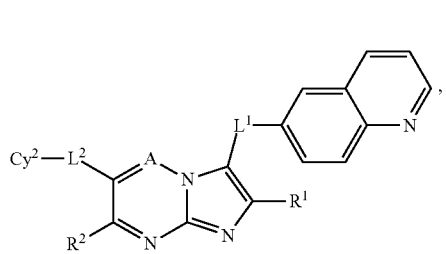

especially wherein
A is CH or N, especially N;
$L^1$ is $(CR^4R^5)_m$ wherein each of $R^4$ and $R^5$, independently of the other, is H or $C_{1-6}$-alkyl and m is 0, 1 or 2,
$L^2$ is $(CR^7R^8)_r$ wherein each of $R^7$ and $R^8$, independently of the other, is H or $C_{1-6}$-alkyl and r is 0, 1 or 2,
$R^1$ is H, halo or $C_{1-6}$-alkyl;
$R^2$ is H, halo or $C_{1-6}$-alkyl; and
$Cy^2$ is aryl, especially phenyl, where said aryl or phenyl is unsubstituted or substituted by one to 3 moieties independently selected from the group consisting of —C(=O)—$NR^{c2}R^{d2}$ and halo, wherein $R^{c2}$ and $R^{d2}$ are independently selected from H, $C_{1-10}$-alkyl and $C_{1-6}$ haloalkyl;
where the compounds may also or alternatively be present in the form of a pharmaceutically acceptable salt.

Especially preferred of the group of compounds of the formula III is that with the name 2-fluoro-N-methyl-4-[(7-quinolin-6-yl-methyl)-imidazo[1,2-b]triazin-2-yl]benz-amide (also named Cpd. B hereinafter) which has the formula

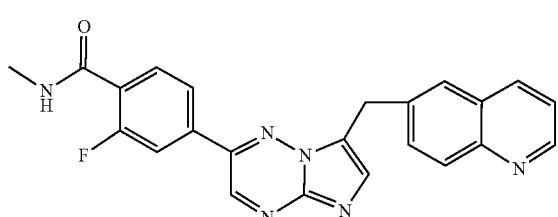

See WO 2008/064157, Example 7. This is the most preferred MET tyrosine kinase inhibitor.

While the two MET inhibitors (Compound A and Compound B) mentioned above are of particular interest, also other MET inhibitors are included in the scope of the present invention.

Such other MET inhibitors (which also includes compounds or antibodies active against HGF) are, for example, selected from the following (including their pharmaceutically acceptable salts, and prodrugs thereof):

Crizotinib (Pfizer) (aka PF02341066) (a highly preferred compound) which has the formula

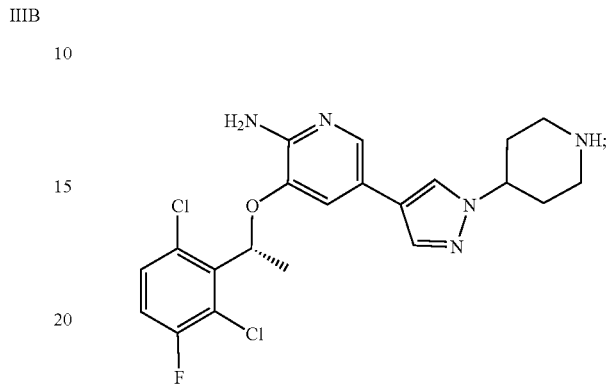

cabozantinib (Exelixis) (aka XL-184) (a highly preferred compound) which has the formula

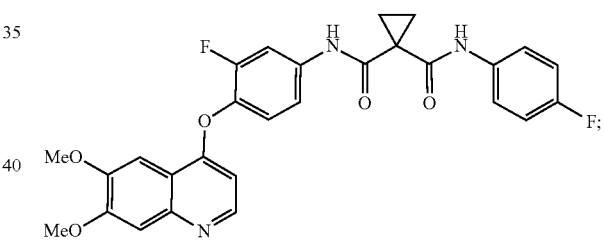

tivatinib (ArQule, daiichi, Kyowa) (aka ARQ-197) (a highly preferred compound) which has the formula

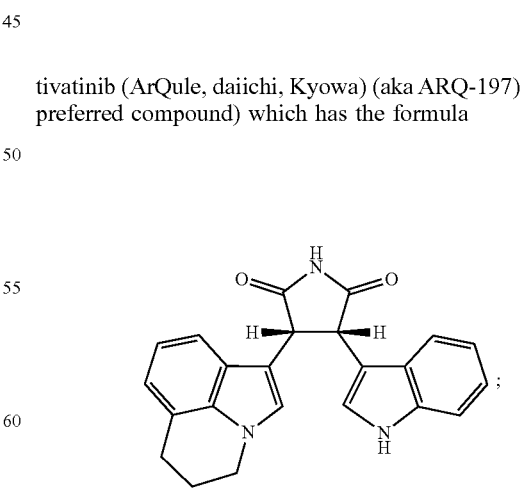

foretinib (Exelixis, GlaxoSmithKline) (aka XL-880) (a highly preferred compound) which has the formula

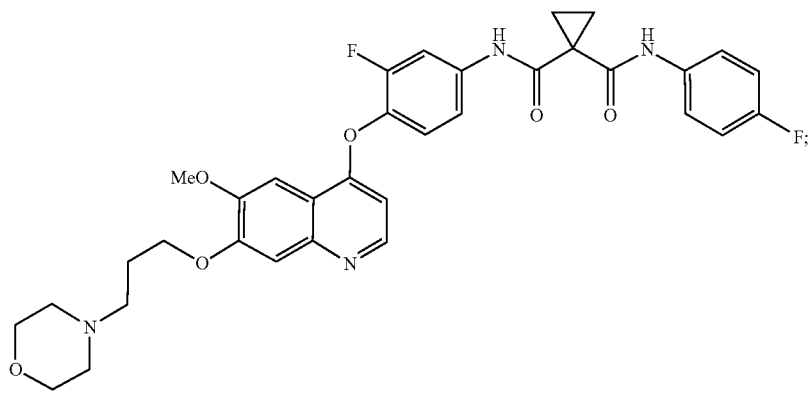 [SMILES: COc1cc2c(Oc3ccc(NC(=O)C4(C(=O)Nc5ccc(F)cc5)CC4)cc3F)ccnc2cc1OCCCN1CCOCC1]
MGCD-265 (MethylGene) (a highly preferred compound) which has the formula
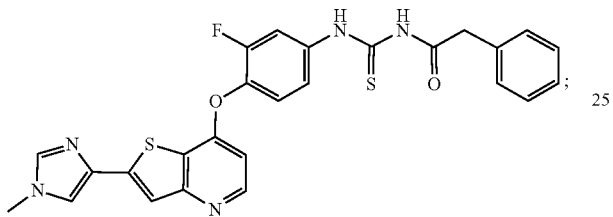
AMG-208 (Amgen) (see also WO 2008/008539) which has the formula
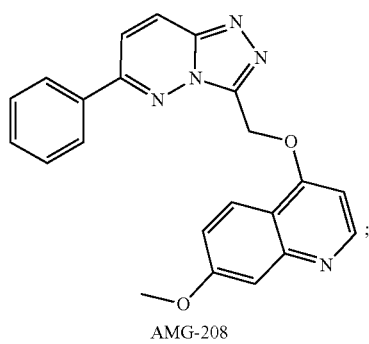
AMG-337 (Amgen);
JNJ-38877605 (Johnson & Johnson) (aka BVT051) (see also WO 2007/075567) which has the formula
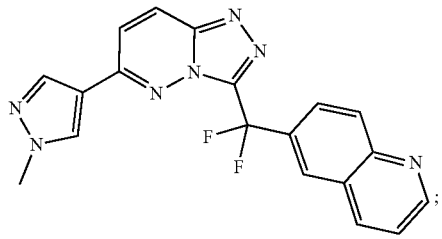
JNJ-38877605
BVT051
MK-8033 (Merck & Co) which has the formula
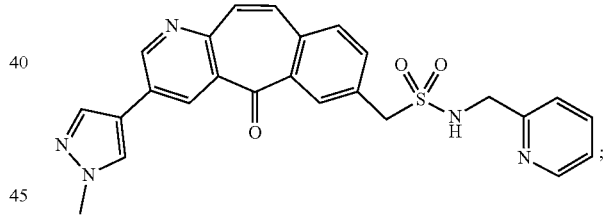
E-7050 (Eisai) which has the formula
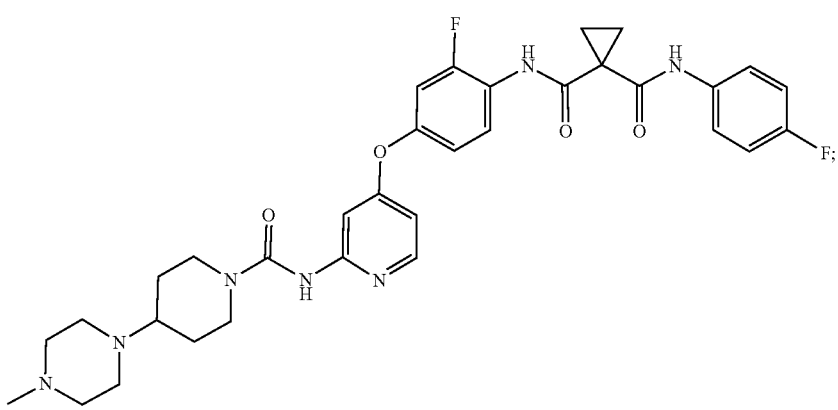 [SMILES: CN1CCN(C2CCN(C(=O)Nc3cc(Oc4ccc(NC(=O)C5(C(=O)Nc6ccc(F)cc6)CC5)c(F)c4)ccn3)CC2)CC1]

EMD-1204831 (Merck Serono);
EMD-1214063 (Merck Serono) (see also WO 2007/019933) which has the formula

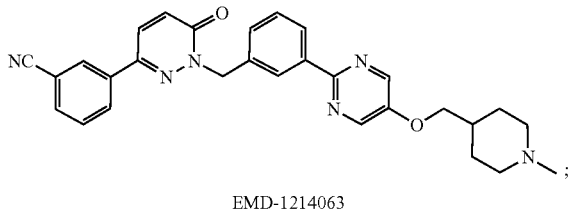 [SMILES: CN1CCC(COc2cnc(-c3cccc(Cn4nc(-c5cccc(C#N)c5)ccc4=O)c3)nc2)CC1]

EMD-1214063 amuvatinib (SuperGen) (aka MP-470) which has the formula

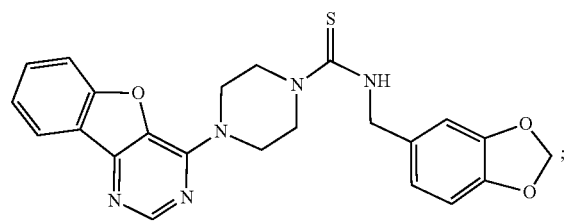 [SMILES: S=C(NCc1ccc2c(c1)OCO2)N1CCN(c2ncnc3c2oc2ccccc23)CC1]

LY-2875358 (Eli Lilly);
BMS-817378 (BristolMyersSquibb, Simcere) which has the formula

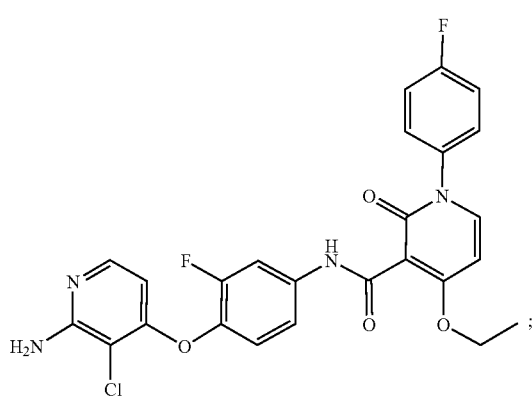 [SMILES: CCOc1ccn(-c2ccc(F)cc2)c(=O)c1C(=O)Nc1ccc(Oc2ccnc(N)c2Cl)c(F)c1]

DP-3590 (Deciphera);
ASP-08001 (Suzhou Ascepion Pharmaceuticals);
HM-5016504 (Hutchison Medipharma);
PF-4217903 (Pfizer) (see also US2007/0265272) which has the formula

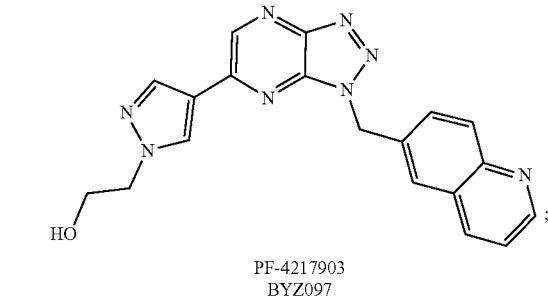

PF-4217903
BYZ097 or
SGX523 (SGX) (see also WO 2008/051808) which has the formula

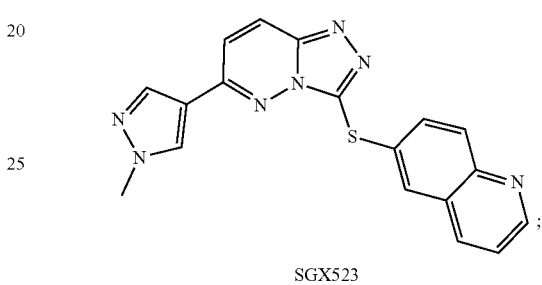

SGX523 or antibodies or related molecules, e.g.
ficlatuzumab (AVEO) monoclonal antibody against HGF (preferred); onartuzumab (Roche) monoclonal antibody against MET (preferred); rilotuzumab (Amgen) monoclonal antibody against HGF (preferred); Tak-701 (Takeda) monoclonal antibody against HGF); LA-480 (Eli Lilly) monoclonal antibody against MET; and/or LY.2875358 (Eli Lilly) monoclonal antibody against MET.

Among the EGFR tyrosine kinase inhibitors useful according to the invention, those of the quinaolineamine class are to be mentioned, in particular.

Especially, EGFR tyrosine kinase inhibitors disclosed in WO 96/30347 (which is incorporated herein by reference with regard to the generic and specific compounds disclosed therein) are to be mentioned here, as a first group, especially 4-(substituted phenylamino)quinazoline derivatives of the formula

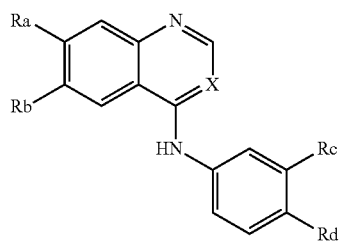

and pharmaceutically acceptable salts and prodrugs thereof, wherein
each Ra, Rb, Rc and Rd is independently selected from hydrogen, halo, hydroxy, amino, hydroxyamino, carboxy, $C_{1-8}$alkoxycarbonyl, nitro, guanidino, ureido, carbamoyl, cyano, trifluoromethyl, $(R^6)_2$N-carbonyl and phenyl-W-alkyl wherein W is selected from a single bond, O, S and NH;

or each Ra or Rb is independently selected from cyano-$C_{1-8}$alkyl and R9 wherein R9 is selected from the group consisting of R5, R5O, (R5)$_2$N, R7C(═O), R5ONH, A and R5Y; wherein
R5 is $C_{1-8}$alkyl;
R6 is hydrogen or R5 wherein the R5s if more than one is present are the same or different;
R7 is R5, R5O or (R6)$_2$N;
A is selected from piperidino, morpholino, pyrrolidino and 4-R6-piperazin-1-yl, imidazol-1-yl, 4-pyridon-1-yl, carboxy-$C_{1-8}$alkyl, phenoxy, phenyl, phenylsulfanyl, $C_{2-8}$alkenyl, (R5)$_2$N-carbonyl-$C_{1-8}$alkyl; and
Y is selected from S, SO, $SO_2$; the alkyl moieties in R5, R5O and (R5)$_2$N are optionally substituted with halo or R9 wherein R9 is defined as above, and wherein the resulting groups are optionally substituted with halo or R9 with the proviso that a nitrogen, oxygen or sulfur atom and another heteroatom can not be attached to the same carbon atom, and with the further proviso that Ra and Rb may not comprise more than three R9 units;
or each Ra or Rb is independently selected from R5-sulfonylamino, phthalimido-$C_{1-8}$alkylsulfonylamino, benzamido, benzenesulfonylamino, 3-phenylureido, 2-oxopyrrolidin-1-yl, 2,5-dioxopyrrolidin-1-yl, and R10-$C_{2-4}$alkanoylamino wherein R10 is selected from halo, R5O, $C_{2-4}$alkanoyloxy, B7C(═O) and (R6)$_2$N; and wherein said benzamido or benzenesulfonylamino or phenyl or phenoxy or anilino or phenylsulfanyl substituent in Ra or Rb may optionally bear one or two halogens, $C_{1-8}$alkyl, cyano, methansulfonyl or $C_{1-8}$alkoxy substituents;
or any two Ra and Rb taken together with the carbons to which they are attached comprise a 5-8 membered ring comprising at least one or two heteroatoms selected from oxygen, sulfur or nitrogen; and wherein the alkyl groups and alkyl portions of the alkoxy or alkylamino groups may be straight chained or if comprised of at least three carbons may be branched or cyclic; each Rc and Rd is independently selected from hydrogen, optionally substituted $C_{1-8}$alkyl, optionally substituted amino, halo, hydroxy, optionally substituted hydroxy; or from azido or R11-ethynyl wherein R11 is selected from hydrogen, optionally substituted $C_{1-8}$alkyl wherein the substituents are selected from hydrogen, amino, hydroxy, R5O, R5NH and (R5)$_2$N;
and X is N or C(CN), with the proviso that a substituent $R^5$ may not comprise another substitutent $R^5$; especially the compound of the formula

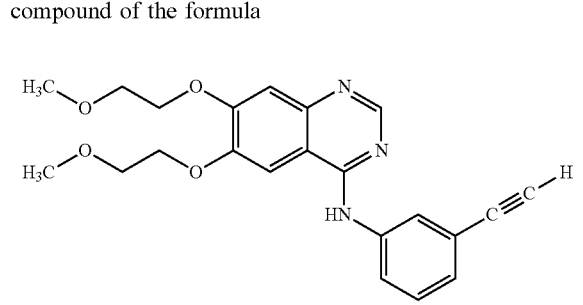

with the INN name erlotinib (marketed in Tarceva®, Roche, Basel, Switzerland)═N-(3-ethinylphenyl)-6,7-bis-(2-methoxyethoxy)quinazolin-4-amine, or a pharmaceutically acceptable salt thereof. Said compound and its manufacture are disclosed e.g. in WO 9630347, Example 20.

Especially, EGFR tyrosine kinase inhibitors disclosed in WO 96/33980 or U.S. Pat. No. 5,616,582 (which are incorporated herein by reference with regard to the generic and specific compounds disclosed therein) are to be mentioned here, as a second group, especially 4-(substituted phenylamino)quinazoline derivatives of the formula

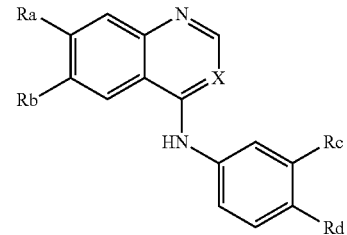

wherein
X is N;
Ra is $C_{1-8}$alkyloxy;
Rb is di-($C_{1-8}$alkyl)-amino-$C_{1-8}$alkoxy, pyrrolidin-1-yl-$C_{1-8}$alkoxy, piperidino-$C_{1-8}$alkoxy, morpholino-$C_{1-8}$alkoxy, piperazin-1-yl-$C_{1-8}$alkoxy, 4-$C_{1-8}$alkylpiperazin-1-yl-$C_{1-8}$alkoxy, imidazol-1-yl-$C_{1-8}$alkoxy, di-($C_{1-8}$alkoxy-$C_{1-8}$alkyl)-amino-$C_{1-8}$alkoxy, thiomorpholino-$C_{1-8}$alkoxy, 1-oxothiomorpholino-$C_{1-8}$alkoxy or 1,1-dioxothiomorpholino-$C_{1-8}$alkoxy, and wherein any of the above-mentioned Rb substituents comprising a $CH_2$ (methylene) group which is not attached to a N or O atom optionally bears on said $CH_2$ group a hydroxy substituent;
and each of Rc and Rd is independently of the other halo, trifluoromethyl or $C_{1-8}$alkyl;
or a pharmaceutically acceptable salt or prodrug thereof, most especially the compound of the formula

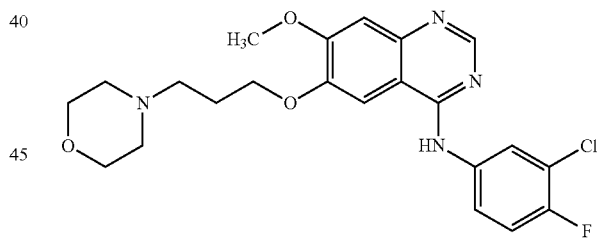

with the INN name gefitinib (marketed in Iressa®, AstraZeneca)═N-(3-hloro-4-fluorophenyl)-7-methoxy-6-[3-(morpholin-4-yl)propoxy]quinazolin-4-amine, or a pharmaceutically acceptable salt thereof, see W═96/33980, Example 1. This compound or its pharmaceutically acceptable salts are especially preferred in the embodiments of the present invention.

Especially, EGFR tyrosine kinase inhibitors disclosed in U.S. Pat. Nos. 6,391,874, 7,157,466, 6,828,320, 6,713,485 and in particular U.S. Pat. No. 6,727,256 (═WO9935146) (which are incorporated herein by reference with regard to the generic and specific compounds disclosed therein) are to be mentioned here, as a third group, especially 4-(substituted phenylamino)quinazoline derivatives of the formula

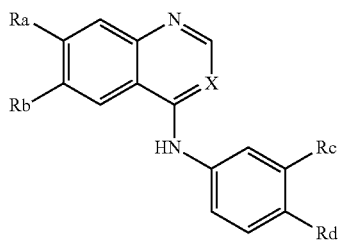

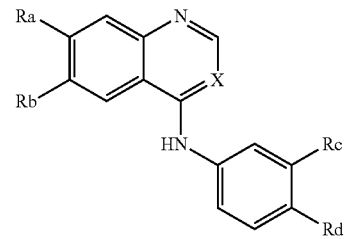

wherein X is N;
one of Ra and Rb is a group $CH_3SO_2CH_2CH_2NHCH_2$—Ar—, wherein Ar is selected from phenyl, furanyl, thiophenyl, pyrrolyl and thiazolyl, each of which may optionally be substituted by one or two substituents selected from the group consisting of one or two halo, $C_{1-8}$alkyl and $C_{1-8}$alkoxy; the other of Ra and Rb is selected from the group consisting of hydrogen, halo, hydroxy, $C_{1-8}$ alkyl, $C_{1-8}$alkoxy, $C_{1-8}$alkylamino and di($C_{1-8}$alkyl)amino;
one of Rc and Rd represents benzyl, halo-, dihalo- or trihalobenzyl, trihalomethylbenzyl, benzoyl, pyridylmethyl, pyridylmethoxy, phenoxy, benzyloxy, halo-, dihalo- or trihalobenzyloxy, trihalomethylbenzyloxy, benzenesulphonyl or hydrogen;
the other of Rc and Rd is hydrogen or hydroxy, halo, $C_{1-8}$alkyl, $C_{2-8}$alkenyl, $C_{2-8}$alkynyl, $C_{1-8}$alkoxy, amino, $C_{1-8}$alkylamino, di($C_{1-8}$alkyl)amino, $C_{1-8}$alkylthio, $C_{1-8}$alkylsulphinyl, $C_{1-8}$ alkylsulphonyl, $C_{1-8}$alkylcarbonyl, carboxyl, carbamoyl, $C_{1-8}$alkoxycarbonyl, $C_{1-8}$alkanoylamino, N—($C_{1-8}$alkyl)carbamoyl, N,N-di($C_{1-8}$alkyl)carbamoyl, cyano, nitro or trifluoromethyl;
or a pharmaceutically acceptable salt or prodrug thereof, more especially the compound of the

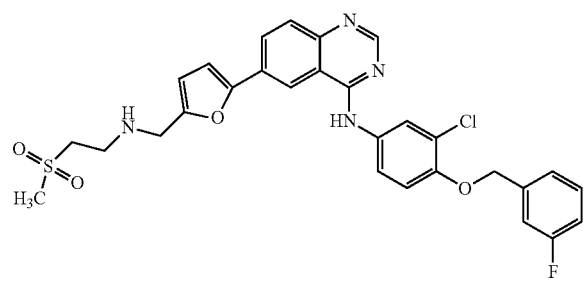 [SMILES: CS(=O)(=O)CCNCc1ccc(-c2ccc3ncnc(Nc4ccc(OCc5cccc(F)c5)c(Cl)c4)c3c2)o1]

with the INN name lapatinib (marketed in Tykerb® (USA), Tyverb® (EP), GlaxoSmithKline) with the name N-[3-chloro-4-(3-fluorobenzyloxy)phenyl]-6-{5-[4-(methylsulfonyl)-2-azabutyl]-2-furyl}quinazolin-4-amine, or a pharmaceutically acceptable salt or prodrug thereof, see e.g. WO9935146 (Example 29).

Especially, EGFR tyrosine kinase inhibitors disclosed in WO97/38983 or especially WO2000031048 (which are incorporated herein by reference with regard to the generic and specific compounds disclosed therein) are to be mentioned here, as a fourth group, especially 4-(substituted phenylamino)quinazoline derivatives of the formula or pharmaceutically acceptable salts or prodrugs thereof, wherein
X is N,
Ra is -D-E-F and Rb is —$SR^{4*}$, halo, —$OR^{4*}$, —$NHR^{3*}$ or hydrogen, or
Rb is -D-E-F and Ra is —$SR^{4*}$, halo, —$OR^{4*}$, —$NHR^{3*}$ or hydrogen,
wherein, respectively,
D is —$N(R^{2*})$—, —O—, —$CH(R^{2*})$—, —$N(R^{2*})$—NH—, —$N(R^{2*})$—O—, —$CH(R^{2*})$—NH—, —$CH(R^{2*})$—O—, —$CH(R^{2*})$—$CH_2$—, —NH—$CH(R^{2*})$—, —O—$CH(R^{2*})$—, —S—$CH(R^{2*})$— or absent;
E is —C(=O)—, —S(=O)$_2$—, —P(=O)(OR$^{2*}$)— or —S(=O)—,
F is —C(R*)=CHR$^{5*}$, —C≡C—R$^{5*}$, or —C(R$^{1*}$)=C=CHR$^{5*}$;
provided that when E is S(=O)$_2$— or —S(=O)—, D is not —NH—$CH(R^{2*})$— or —O—$CH(R^2)$—;
$R^{1*}$ is hydrogen, halogen or $C_{1-8}$alkyl,
$R^{2*}$, $R^{3*}$ and $R^{4*}$ are independently hydrogen, $C_{1-8}$alkyl, —$(CH_2)_{n*}$—N-piperidinyl, —$(CH_2)_{n*}$—N-piperazinyl, —$(CH_2)_{n*}$—$N_1$-piperazinyl($N_4$—$C_{1-8}$alkyl), —$(CH_2)_{n*}$—N-pyrrolidinyl, —$(CH_2)_{n*}$—N-pyridinyl, —$(CH_2)_{n*}$—N-imidazolyl, —$(CH_2)_{n*}$—N-morpholinyl, —$(CH_2)_{n*}$—N-thiomorpholinyl, —$(CH_2)_{n*}$—N-hexohydroazepinyl or substituted $C_{1-8}$alkyl, wherein the substituents are selected from —OH, —$NH_2$, or —N(B*)(A*), wherein A* and B* are independently hydrogen, $C_{1-8}$alkyl, —$(CH_2)_{n*}$—OH, —$(CH_2)_{n*}$—N-piperidinyl, —$(CH_2)_{n*}$—N-piperazinyl, —$(CH_2)_{n*}$—$N_1$-piperazinyl($N_4$—$C_{1-8}$alkyl), —$(CH_2)_{n*}$—N-pyrrolidinyl, —$(CH_2)_{n*}$—N-pyridyl and —$(CH_2)_{n*}$—N-imidazolyl;
Rc and Rd are independently hydrogen, halo, $C_{1-8}$alkyl, $C_{3-8}$cycloalkyl, $C_{1-8}$alkoxy, $C_{3-8}$cycloalkoxy, nitro, $C_{1-8}$perfluoroalkyl, hydroxy, $C_{1-8}$acyloxy, amino, —NH($C_{1-8}$alkyl), —N($C_{1-8}$alkyl)$_2$, —NH($C_{3-8}$cycloalkyl), —NH($C_{3-8}$cycloalkyl)$_2$, hydroxymethyl, $C_{1-8}$acyl, cyano, azido, $C_{1-8}$thioalkyl, $C_{1-8}$sulfinylalkyl, $C_{1-8}$sulfonylalkyl, $C_{3-8}$thiocycloalkyl, $C_{3-8}$sulfinylcycloalkyl, $C_{3-8}$sulfonylcycloalkyl, mercapto, $C_{1-8}$alkoxycarbonyl, $C_{3-8}$cycloalkoxycarbonyl, $C_{2-8}$alkenyl, $C_{4-8}$cycloalkenyl, or $C_{2-8}$alkynyl;
$R^{5*}$ is hydrogen, halo, $C_{1-6}$perfluoroalkyl, 1,1-difluoro-$C_{1-6}$alkyl, $C_{1-6}$alkyl, —$(CH_2)_{n*}$—N-piperidinyl, —$(CH_2)_{n*}$—N-piperazinyl, —$(CH_2)_{n*}$—$N_1$-piperazinyl($N_4$—$C_{1-8}$alkyl), —$(CH_2)_{n*}$—N-pyrrolidinyl, —$(CH_2)_{n*}$—N-pyridyl, —$(CH_2)_{n*}$—N-imidazolyl, —$(CH_2)_{n*}$—N-morpholinyl, —$(CH_2)_{n*}$—N-thiomorpholinyl, —CH=$CH_2$, —CH=CH—$C_{1-8}$alkyl, —$(CH_2)_{n*}$—N-hexahydroazepinyl, —$(CH_2)_{n*}$—$NH_2$, —$(CH_2)_{n*}$—NH—$(C_{1-3})$alkyl, —$(CH_2)_{n*}$—N($C_{1-8}$alkyl)$_2$, -1-oxo-$C_{1-8}$alkyl, carboxy, $C_{1-8}$alkoxycarbonyl, N—$C_{1-8}$alkyl-carbamoyl, phenyl or substituted phenyl, wherein the phenyl can have from one to three substituents independently selected from Rc and Rd or a monocyclic heteroaryl group selected from the group consisting of pyridyl, thienyl and imidazolyl, and each $C_{1-8}$alkyl group above in $R^{5*}$ can be substituted with —OH, —NH$_2$ or NA*B*, where A* and B* are as defined above; $R^{6*}$ is hydrogen or $C_{1-8}$alkyl;
and n* is 1 to 8, especially 1 to 4; especially the compound of the formula

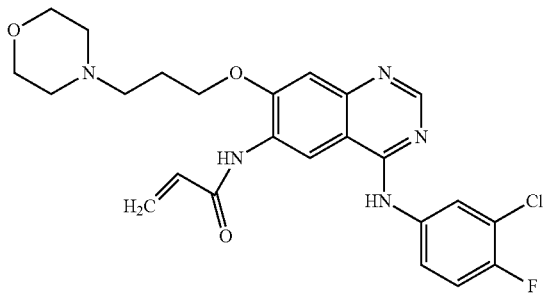 [SMILES: C=CC(=O)Nc1cc2c(Nc3ccc(F)c(Cl)c3)ncnc2cc1OCCCN1CCOCC1]

with the INN name canertinib (Pfizer) (e.g. used as dihydrochloride)) N-[4-[(3-Chloro-4-fluorophenyl)amino]-7-(3-morpholin-4-ylpropoxy)quinazolin-6-yl]prop-2-enamide, or a pharmaceutically acceptable salt or prodrug thereof, see especially WO2000031048.

Especially, EGFR tyrosine kinase inhibitors disclosed in WO2005028443 (which is incorporated herein by reference with regard to the generic and specific compounds disclosed therein) are to be mentioned here, as a fifth group, especially 4-(substituted phenylamino)quinazoline derivatives of the formula

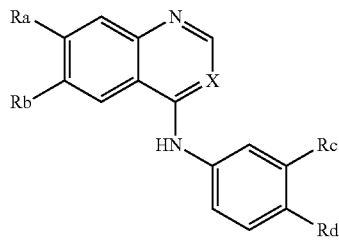

wherein X is C—CN;
Ra is $C_{1-8}$alkoxy;
Rb is amino- or N—[N'-mono- or N',N'-di($C_{1-8}$alkyl)]amino}-$C_{4-8}$alkenoyl)-amino;
Rc is halo or $R_2$—(CH$_2$)$_{n}$—$R_3$**—
wherein $R_2$ is a pyridyl, thiophenyl, pyrimidinyl, thiazolyl or phenyl, each optionally substituted with up to three substituents selected from $C_{1-8}$alkyl, $C_{1-8}$alkoxy and halogen, $R_3$ is —O— or —S— and n** is 0 to 8, preferably 0 or 1;
and Rd is halo;
or a pharmaceutically acceptable salt or prodrug thereof, especially the compound of the formula

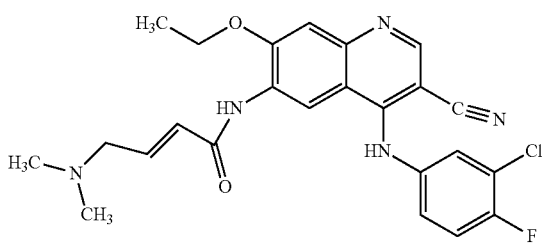 [SMILES: CCOc1cc2ncc(C#N)c(Nc3ccc(F)c(Cl)c3)c2cc1NC(=O)/C=C/CN(C)C]

with the INN name pelitinib (Wyeth, owned by Pfizer) with the name 2E)-N-[4-[(3-Chloro-4-fluorophenyl)amino]-3-cyano-7-ethoxy-6-quinolinyl]-4-(dimethylamino)-2-butenamide, see WO2005028443 (Example 20), or the compound of the formula

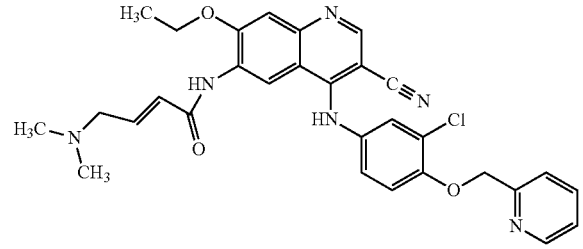 [SMILES: CCOc1cc2ncc(C#N)c(Nc3ccc(OCc4ccccn4)c(Cl)c3)c2cc1NC(=O)/C=C/CN(C)C]

with the INN name neratinib (Pfizer Inc.), (2E)-N-[4-[[3-chloro-4-[(pyridin-2-yl)methoxy]phenyl]amino]-3-cyano-7-ethoxyquinolin-6-yl]-4-(dimethylamino)but-2-enamide, see e.g. WO2005028443 Example 2;
or a pharmaceutically acceptable salt or prodrug thereof, respectively.

Among the possible EGFR inhibitors, also antibodies may be mentioned, e.g. Cetuximab (Erbitux®) (ImClone Systems, Bristol-Myers Squibb and Merck KgaA) which is a chimeric (mouse/human) monoclonal antibody, active as an epidermal growth factor receptor (EGFR) inhibitor, which can be administered e.g. intravenously.

A particular embodiment of the invention embodiments in each case relates to the EGFR inhibitors of the formula

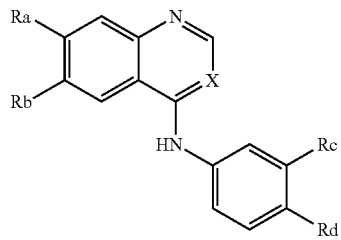

wherein
X is N or C(CN);
Ra is selected from the group consisting of $C_{1-8}$alkyloxy or ($C_{1-8}$alkyloxy, 1-piperidin-1-yl, 1-piperazin-1-yl, 4-$C_{1-8}$alkyl-piperazin-1-yl, morpholin-1-yl, thiomorpholino-1-yl, S-oxothiomorpholin-1-yl or S,S-dioxothiomorpholinyl-1-yl)-$C_{1-8}$alkyloxy;
Rb is selected from $C_{3-8}$alkenoyl, {amino- or N—[N'-mono- or N',N'-di($C_{1-8}$alkyl)]amino}-$C_{4-8}$alkenoyl)-amino, [($C_{1-8}$alkylsulfonyl-$C_{1-8}$alkylamino)-$C_{1-8}$alkyl]-furyl or ($C_{1-8}$alkyloxy, 1-piperidin-1-yl, 1-piperazin-1-yl, 4-$C_{1-8}$alkyl-piperazin-1-yl, morpholin-1-yl, thiomorpholin-1-yl, S-oxothiomorpholin-1-yl or S,S-dioxothiomorpholinyl-1-yl)-$C_{1-8}$alkyloxy;
Rc is halo or $C_{2-8}$alkynyl; and
Rd is hydrogen, pyridinyl-$C_{1-8}$alkyloxy or unsubstituted or halogen substituted phenyl-$C_{1-8}$alkyloxy;
especially wherein:
X is N or C(CN);
Ra is methoxy, ethoxy, 3-morpholinopropyloxy or 2-methoxyethoxy;
Rb is 4-(dimethylamino)-but-2-enoylamino, prop-2-enoylamino, 5-[(2-methylsulfonyl-ethyl)-aminomethyl]-furan-2-yl, 2-methoxyethoxy or 3-morpholinopropoxy;

Rc is chloro or ethynyl; and
Rd is hydrogen, fluoro, pyridin-2-ylmethoxy or 3-fluorophenyl-methoxy;
or a pharmaceutically acceptable salt or prodrug thereof, respectively.

If not mentioned otherwise, the following definitions serve to define more general expressions used above and below by specific variants, thus defining more particular invention embodiments wherein one, more than one or all general expressions are defined by these following definitions:

In the preceding and following definitions, $C_{1-8}$ is preferably $C_{1-6}$, more preferably $C_{1-4}$, meaning a linear or branched moiety with 1 to 8, 1 to 6 or 1 to 4 carbon atoms, respectively.

In the preceding and following definitions, $C_{2-8}$ is preferably $C_{2-6}$, more preferably $C_{2-4}$, meaning a linear or branched moiety with 2 to 8, 2 to 6 or 2 to 4 carbon atoms, respectively.

In the preceding and following definitions, $C_{3-8}$ is preferably $C_{3-6}$, more preferably $C_{3-4}$, meaning moiety with 3 to 8, 3 to 6 or 3 to 4 carbon atoms, respectively.

In the preceding and following definitions, $C_{4-8}$ is preferably $C_{4-6}$, more preferably $C_4$, meaning a linear or branched moiety with 4 to 8, 4 to 6 or 4 carbon atoms, respectively.

"Lower" refers to a group with up to 8, especially up to 6 carbon atoms, if not defined otherwise. For example, lower alkyl refers to $C_{1-8}$ alkyl, e.g. $C_{1-6}$ alkyl, such as methyl, ethyl, n-propyl, isopropyl, n-butyl, sec-butyl, isobutyl or tert-butyl.

At various places in the present specification, substituents of compounds useful according to the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds useful according to the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" (also in alkoxy, arylalkyl, heteroarylalkyl, haloalkyl or the like) is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, the term "alkylyene" refers to a linking alkyl group.

As used herein, "alkenyl" refers to an alkyl group having one or more double carbon-carbon bonds. Example alkenyl groups include ethenyl, propenyl, and the like.

As used herein, "alkenylene" refers to a linking alkenyl group.

As used herein, "alkynyl" refers to an alkyl group having one or more triple carbon-carbon bonds. Example alkynyl groups include ethynyl, propynyl, and the like.

As used herein, "alkynylene" refers to a linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "arylene" refers to a linking aryl group.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like.

As used herein, "cycloalkylene" refers to a linking cycloalkyl group.

As used herein, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heteroarylene" refers to a linking heteroaryl group.

As used herein, "heterocycloalkyl" or "heterocyclyl" refers to a non-aromatic heterocycle where one or more of the ring-forming atoms is a heteroatom such as an O, N, or S atom. Heterocycloalkyl groups can include mono- or polycyclic (e.g., having 2, 3 or 4 fused rings) ring systems as well as spirocycles. Example "heterocycloalkyl" groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles. A heterocycloalkyl group having one or more fused aromatic rings can be attached though either the aromatic or non-aromatic portion. Also included in the definition of heterocycloalkyl are moieties where one or more ring-forming atoms is substituted by 1 or 2 oxo or sulfido groups. In some embodiments, the heterocycloalkyl group has from 1 to about 20 carbon atoms, and in further embodiments from about 3 to about 20 carbon atoms. In some embodiments, the heterocycloalkyl group contains 3 to about 20, 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "heterocycloalkylene" refers to a linking heterocycloalkyl group.

As used herein, "biaryl" refers to an aryl group substituted by another aryl group.

As used herein, "biheteroaryl" refers to a heteroaryl group substituted by another heteroaryl group.

As used herein, "halo" or "halogen" includes fluoro, chloro, bromo, and iodo.

As used herein, "alkoxy" refers to an —O-alkyl group. Example alkoxy groups include methoxy, ethoxy, propoxy (e.g., n-propoxy and isopropoxy), t-butoxy, and the like.

As used herein, "acyl" includes an organic radical corresponding to the residue of, for example, an organic acid from which the hydroxyl group has been removed, i.e., a radical having the formula $R^A$—C(O)— where $R^A$ may in particular be aliphatic or substituted aliphatic, or it may for example be a substituted or unsubstituted mono- or bi-cyclic ring. Thus, R may be selected from lower $C_1$-$C_6$ alkyl, $C_3$-$C_7$ cycloalkyl, phenyl, benzyl or phenethyl group. Amongst others, exemplary acyl is alkyl-carbonyl. Examples of acyl groups, include, but are not limited to, acetyl, propionyl and butyryl. Lower acyl is for example formyl or lower alkylcarbonyl, in particular acetyl.

The MET and FGFR inhibitors can be manufactured as described in the patent applications and patents mentioned above, which are also incorporated by reference especially with regard to their manufacturing methods.

Compounds useful according to the invention can also include all isotopes of atoms occurring in the intermediates or final compounds. Isotopes include those atoms having the same atomic number but different mass numbers. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}P$, $^{32}P$, $^{35}S$, $^{36}Cl$, $^{125}I$ respectively. Various isotopically labeled compounds of the present invention, for example those into which radioactive isotopes such as $^3H$, $^{13}C$, and $^{14}C$ are incorporated. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT) including drug or substrate tissue distribution assays, or in radioactive treatment of patients. In particular, an $^{18}F$ or labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium, for example in the ranges given above.

Isotopically-labeled MET and/or EGFR tyrosine kinase inhibitor compounds forming part of a combination product according to the invention can generally be prepared by conventional techniques known to those skilled in the art or by processes analogous to those described in the accompanying Examples and Preparations using an appropriate isotopically-labeled reagents in place of the non-labeled reagent previously employed.

The present invention embodiments also include pharmaceutically acceptable salts of the compounds useful according to the invention described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes prodrugs of the compounds useful according to the invention. As used herein, "prodrugs" refer to any covalently bonded carriers which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

The compounds useful according to the invention (=being included in a combination, especially a combination product, according to the invention, respectively, or being used according to the invention, optionally also including further co-agents as defined below, that is, all active ingredients), as well as their pharmaceutically acceptable salts or prodrugs, can also be present as tautomers, N-oxides or solvates, e.g. hydrates. All these variants, as well as any single one thereof or combination of two or more to less than all such variants, are encompassed and to be read herein where a compound included in the inventive combination products, e.g. an EGFR tyrosine kinase inhibitor and/or a MET tyrosine kinase inhibitor, is mentioned.

The present invention, according to a first embodiment mentioned above and below, relates to a pharmaceutical combination, especially a pharmaceutical combination product, comprising the mentioned combination partners and at least one pharmaceutically acceptable carrier.

"Combination" refers to formulations of the separate partners with or without instructions for combined use or to combination products. The combination partners may thus be entirely separate pharmaceutical dosage forms or pharmaceutical compositions that are also sold independently of each other and where just instructions for their combined use are provided in the package equipment, e.g. leaflet or the like, or in other information e.g. provided to physicians and medical staff (e.g. oral communications, communications in writing or the like), for simultaneous or sequential use for being jointly active, especially as defined below.

"Combination product" refers especially to either a fixed combination in one dosage unit form, or a kit of parts for the combined administration where an EGFR tyrosine kinase inhibitor and a MET tyrosine kinase inhibitor (and optionally yet a further combination partner (e.g. an other drug as explained below, also referred to as "co-agent") may be administered independently at the same time or separately within time intervals, especially where these time intervals allow that the combination partners show a cooperative (=joint), e.g. synergistic effect. The terms "coadministration" or "combined administration" or the like as utilized herein are meant to encompass administration of the selected combination partner to a single subject in need thereof (e.g. a patient), and are intended to include treatment regimens in which the agents are not necessarily administered by the same route of administration and/or at the same time.

The term "combination product" as used herein thus means a pharmaceutical product that results from the mixing or combining of more than one active ingredient and includes both fixed and non-fixed combinations of the active ingredients (which may also be combined).

The term "fixed combination" means that the active ingredients, e.g. an EGFR tyrosine kinase inhibitor and MET tyrosine kinase inhibitor, are both administered to a patient simultaneously in the form of a single entity or dosage. In other terms: the active ingredients arepresent in one dosage form, e.g. in one tablet or in one capsule.

The term "non-fixed combination" means that the active ingredients are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients. The term "non-fixed combination" thus defines especially a "kit of parts" in the sense that the combination partners (i) EGFR tyrosine kinase inhibitor and (ii) MET tyrosine kinase inhibitor (and if present further one or more co-agents) as defined herein can be dosed independently of each other or by use of different fixed combinations with distinguished amounts of the combination partners, i.e. simultaneously or at different time points, where the combination partners may also be used as entirely separate pharmaceutical dosage forms or pharmaceutical formulations that are also sold independently of each other and just instructions of the possibility of their combined use is or are provided in the package equipment, e.g. leaflet or the like, or in other information e.g. provided to physicians and medical staff. The independent formulations or the parts of the kit of parts can then, e.g. be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (i) and (ii), thus being jointly active. The ratio of the total amounts of the combination partner (i) to the combination partner (ii) to be administered in the combined preparation can be varied, e.g. in order to cope with the needs of a patient sub-population to be treated or the needs of the single patient which different needs can be due to age, sex, body weight, etc. of the patients.

The invention also relates to (i) a MET inhibitor and (ii) an EGFR inhibitor, or a pharmaceutically acceptable salt thereof, for combined use in a method of treating an EGFR tyrosine kinase activity and/or MET tyrosine kinase activity mediated disease, especially a cancer.

In a further embodiment, the MET inhibitor and the EGFR inhibitor for use according to the preceding paragraph are selected as follows: the MET tyrosine kinase inhibitor is selected from the group consisting of (E)-2-(1-(3-((7-fluoroquinolin-6-yl)methyl)imidazo[1,2-b]pyridazin-6-yl)ethylidene)hydrazinecarboxamide and/or (especially or) 2-fluoro-N-methyl-4-[(7-quinolin-6-yl-methyl)-imidazo[1,2-b]triazin-2-yl]benzamide, or a pharmaceutically acceptable salt or prodrug thereof, respectively, and the EGFR inhibitor is gefinitib and/or (especially or) elotinib, or a pharmaceutically acceptable salt or prodrug thereof.

The combination partners (i) and (ii) in any invention embodiment are preferably formulated or used to be jointly (prophylactically or especially therapeutically) active. This means in particular that there is at least one beneficial effect, e.g. a mutual enhancing of the effect of the combination partners (i) and (ii), in particular a synergism, e.g. a more than additive effect, additional advantageous effects (e.g. a further therapeutic effect not found for any of the single compounds), less side effects, a combined therapeutic effect in a non-effective dosage of one or both of the combination partners (i) and (ii), and very preferably a clear synergism of the combination partners (i) and (ii).

For example, the term "jointly (therapeutically) active" may mean that the compounds may be given separately or sequentially (in a chronically staggered manner, especially a sequence-specific manner) in such time intervals that they preferably, in the warm-blooded animal, especially human, to be treated, and still show a (preferably synergistic) interaction (joint therapeutic effect). A joint therapeutic effect can, inter alia, be determined by following the blood levels, showing that both compounds are present in the blood of the human to be treated at least during certain time intervals, but this is not to exclude the case where the compounds are jointly active although they are not present in blood simultaneously.

The present invention thus pertains to a combination product for simultaneous, separate or sequential use, such as a combined preparation or a pharmaceutical fixed combination, or a combination of such preparation and combination.

In the combination therapies of the invention, the compounds useful according to the invention may be manufactured and/or formulated by the same or different manufacturers. Moreover, the combination partners may be brought together into a combination therapy: (i) prior to release of the combination product to physicians (e.g. in the case of a kit comprising the compound of the invention and the other therapeutic agent); (ii) by the physician themselves (or under the guidance of a physician) shortly before administration; (iii) in the patient themselves, e.g. during sequential administration of the compound of the invention and the other therapeutic agent.

In certain embodiments, any of the above methods involve further administering one or more other (e.g. third) co-agents, especially a chemotherapeutic agent.

Thus, the invention relates in a further embodiment to a combination product, particularly a pharmaceutical composition, comprising a therapeutically effective amount of (i) an EGFR tyrosine kinase inhibitor and (ii) a MET tyrosine kinase inhibitor, or a pharmaceutically acceptable salt thereof, respectively, and at least one third therapeutically active agent (co-agent), e.g. another compound (i) and/or (ii) or a different co-agent. The additional co-agent is preferably selected from the group consisting of an anti-cancer agent; an anti-inflammatory agent.

Also in this case, the combination partners forming a corresponding product according to the invention may be mixed to form a fixed pharmaceutical composition or they may be administered separately or pairwise (i.e. before, simultaneously with or after the other drug substance(s)). A combination product according to the invention can besides or in addition be administered especially for cancer therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Possible anti-cancer agents (e.g. for chemotherapy) as co-agents include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibittors; mTOR inhibitors; antineoplastic antimetabolites; platin compounds; compounds targeting/decreasing a protein or lipid kinase activity; anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors; kinesin spindle protein inhibitors; MEK inhibitors; leucovorin; EDG binders; antileukemia compounds; ribonucleotide reductase inhibittors; S-adenosylmethionine decarboxylase inhibitors; angiostatic steroids; corticosteroids; other chemotherapeutic compounds (as defined below); photosensitizing compounds.

Further, alternatively or in addition combination products according to the invention may be used in combination with other tumor treatment approaches, including surgery, ionizing radiation, photodynamic therapy, implants, e.g. with corticosteroids, hormones, or they may be used as radiosensitizers.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole.

The term "antiestrogen" as used herein relates to a compound which antagonizes the effect of estrogens at the estrogen receptor level. The term includes, but is not limited to tamoxifen, fulvestrant, raloxifene and raloxifene hydrochloride.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804).

The term "topoisomerase II inhibitor" as used herein includes, but is not limited to the anthracyclines such as doxorubicin (including liposomal formulation, e.g. CAE-LYX), daunorubicin, epirubicin, idarubicin and nemorubicin, the anthraquinones mitoxantrone and losoxantrone, and the podophillotoxines etoposide and teniposide.

The term "microtubule active compound" relates to microtubule stabilizing, microtubule destabilizing compounds and microtublin polymerization inhibitors including, but not limited to taxanes, e.g. paclitaxel and docetaxel, *vinca* alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof.

The term "alkylating compound" as used herein includes, but is not limited to, cyclophosphamide, ifosfamide, melphalan or nitrosourea (BCNU or Gliadel).

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA). Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl) ethyl]-amino]methyl]phenyl]-2E-2-propenamide, or a pharmaceutically acceptable salt thereof, especially the lactate salt.

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed.

The term "platin compound" as used herein includes, but is not limited to, carboplatin, cis-platin, cisplatinum and oxaliplatin.

The term "compounds targeting/decreasing a protein or lipid kinase activity"; or a "protein or lipid phosphatase activity"; or "further anti-angiogenic compounds" as used herein includes, but is not limited to, c-Met tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

c) compounds targeting, decreasing or inhibiting the activity of the Trk receptor tyrosine kinase family, or ephrin kinase family inhibitors;

d) compounds targeting, decreasing or inhibiting the activity of the Axl receptor tyrosine kinase family;

e) compounds targeting, decreasing or inhibiting the activity of the Ret receptor tyrosine kinase;

f) compounds targeting, decreasing or inhibiting the activity of the Kit/SCFR receptor tyrosine kinase, e.g. imatinib;

g) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/ LY379196; isochinoline compounds such as those disclosed in WO 00/09495; FTIs; PD184352 or QAN697 (a P13K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™) cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF;

m) compounds targeting, decreasing or inhibiting the activity of the Ron receptor tyrosine kinase.

Further anti-angiogenic compounds include compounds having another mechanism for their activity, e.g. unrelated to protein or lipid kinase inhibition e.g. thalidomide (THALOMID) and TNP-470.

The term "Compounds which target, decrease or inhibit the activity of a protein or lipid phosphatase" includes, but is not limited to inhibitors of phosphatase 1, phosphatase 2A, or CDC25, e.g. okadaic acid or a derivative thereof.

The term "Compounds which induce cell differentiation processes" includes, but is not limited to e.g. retinoic acid, α- γ- or δ-tocopherol or α- γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

The term "Compounds which target, decrease or inhibit the activity of FMS-like tyrosine kinase receptors (Flt-3R)" are especially compounds, proteins or antibodies which inhibit members of the Flt-3R receptor kinase family, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG, 17-DMAG), a geldanamycin derivative; other geldanamycin related compounds; radicicol and HDAC inhibitors; IPI-504, CNF1010, CNF2024, CNF1010 from Conforma Therapeutics; temozolomide, AUY922 from Novartis.

The term "antiproliferative antibodies" as used herein includes, but is not limited to erbitux, bevacizumab, rituximab, PR064553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

"Somatostatin receptor antagonists" as used herein refers to compounds which target, treat or inhibit the somatostatin receptor such as octreotide, and SOM230.

"Tumor cell damaging approaches" refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "kinesin spindle protein inhibitors" is known in the field and includes SB715992 or SB743921 from GlaxoSmithKline, pentamidine/chlorpromazine from CombinatoRx.

The term "MEK inhibitors" is known in the field and includes ARRY142886 from Array PioPharma, AZD6244 from AstraZeneca, PD181461 from Pfizer, leucovorin.

The term "ribonucleotide reductase inhibitors" includes, but is not limited to to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF/VEGFR disclosed in WO 98/35958, e.g. 1-(4-chloroanilino)-4-(4-pyridylmethyl) phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab.

"Photodynamic therapy" as used herein refers to therapy which uses certain chemicals known as photosensitizing compounds to treat or prevent cancers. Examples of photodynamic therapy includes treatment with compounds, such as e.g. VISUDYNE and porfimer sodium.

"Angiostatic steroids" as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

"Corticosteroids" as used herein includes, but is not limited to compounds, such as e.g. fluocinolone, dexamethasone; in particular in the form of implants.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

A combination product according to the invention may also be used in combination with or comprise one or more further drug substances selected from the group of anti-inflammatory drug substances; antihistamine drug substances; bronchodilatatory drug substances, NSAID; antagonists of chemokine receptors.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229;

LTB4 antagonists such LY293111, CGS025019C, CP-195543, SC-53228, BIIL 284, ONO 4057, SB 209247 and those described in U.S. Pat. No. 5,451,700; LTD4 antagonists such as montelukast and zafirlukast; PDE4 inhibitors such as cilomilast, Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, especially a compound of formula

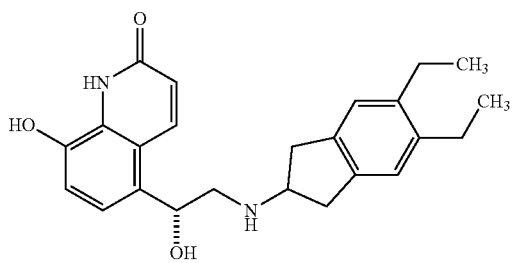 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula I of WO 04/16601, and also compounds of WO 04/033412.

Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in WO 01/04118, WO 02/51841, WO 02/53564, WO 03/00840, WO 03/87094, WO 04/05285, WO 02/00652, WO 03/53966, EP 424021, U.S. Pat. Nos. 5,171,744, 3,714,357, WO 03/33495 and WO 04/018422.

Suitable chemokine receptors include, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

The term "pharmaceutically effective" preferably relates to an amount that is therapeutically or in a broader sense also prophylactically effective against the progression of a disease or disorder as disclosed herein.

The term "a commercial package" as used herein defines especially a "kit of parts" in the sense that the components (a) MET tyrosine kinase inhibitor and (b) FGFR tyrosine kinase inhibitor as defined above and below, and optionally further co-agents, can be dosed independently or by use of different fixed combinations with distinguished amounts of the components (a) and (b), i.e., simultaneously or at different time points. Moreover, these terms comprise a commercial package comprising (especially combining) as active ingredients components (a) and (b), together with instructions for simultaneous, sequential (chronically staggered, in time-specific sequence, preferentially) or (less preferably) separate use thereof in the delay of progression or treatment of a proliferative disease. The parts of the kit of parts can then, e.g., be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b) (as can be determined according to standard methods. The ratio of the total amounts of the combination partner (a) to the combination partner (b) to be administered in the combined preparation can be varied, e.g., in order to cope with the needs of a patient sub-population to be treated or the needs of the single patient which different needs can be due to the particular disease, age, sex, body weight, etc. of the patients. Preferably, there is at least one beneficial effect, e.g., a mutual enhancing of the effect of the combination partners (a) and (b), in particular a more than additive effect, which hence could be achieved with lower doses of each of the combined drugs, respectively, than tolerable in the case of treatment with the individual drugs only without combination, producing additional advantageous effects, e.g., less side effects or a combined therapeutic effect in a non-effective dosage of one or both of the combination partners (components) (a) and (b), and very preferably a strong synergism of the combination partners (a) and (b).

Both in the case of the use of the combination of components (a) and (b) and of the commercial package, any combination of simultaneous, sequential and separate use is also possible, meaning that the components (a) and (b) may be administered at one time point simultaneously, followed by administration of only one component with lower host toxicity either chronically, e.g., more than 3-4 weeks of daily dosing, at a later time point and subsequently the other component or the combination of both components at a still later time point (in subsequent drug combination treatment courses for an optimal effect) or the like.

The combination products according to the present invention are appropriate for the treatment of various diseases that are mediated by, especially depend on, the activity of EGFR and/or MET tyrosine kinase, respectively. They can thus be used in the treatment of any of the diseases that can be treated by EGFR tyrosine kinase inhibitors and MET tyrosine kinase inhibitors.

The term "FGFR tyrosine kinase activity and/or MET tyrosine kinase activity mediated disease" refers especially to a disease in which activity of one or both kinases leads to abnormal activity of the regulatory pathways including one of both kinases, especially where one or both of the kinases is overactive, e.g. due to overexpression, mutation or relative lack of activity of other regulatory pathways in the cell, e.g. where there is amplification, constitutive activation and/or overactivation of preceding or subsequent regulatory elements.

EGFR inhibitors are e.g. useful in the treatment of one or more of the diseases which respond to an inhibition of EGFR activity, especially a neoplastic or tumor disease, especially solid tumor, more especially those cancers in which EGFR kinases are implicated including breast cancer, gastric cancer, lung cancer, cancer of the prostate, bladder cancer and endometrial cancer. Further cancers include cancer of the kidney, liver, adrenal glands, stomach, ovaries, colon, rectum, pancreas, vagina or thyroid, sarcoma, glioblastomas and numerous tumours of the neck and head, as well as leukemias and multiple myeloma. Especially preferred are cancers of breast or ovary; lung cancer, e.g. NSCLC or SCLC; head and neck, renal, colorectal, pancreas, bladder, gastric or prostate cancer; or glioma; in particular, glioma or colon, rectum or colorectal cancer or more particularly lung cancer are to be mentioned. Also diseases dependent on ligands of EGFR, such as EGF; TGF-α; HB-EGF; amphiregulin; epiregulin; betacellulin, are included.

MET inhibitors are e.g. useful in the treatment of MET related diseases, especially cancers that display evidence for simultaneous activation of MET and FGFR, including gene amplification, activating mutations, expression of cognate RTK ligands, phosphorylation of RTKs at residues indicative of activation, e.g. where the cancer is selected from the group consisting of brain cancer, stomach cancer, genital cancer, urinary cancer, prostate cancer, (urinary) bladder cancer (superficial and muscle invasive), breast cancer, cervical cancer, colon cancer, colorectal cancer, glioma (including glioblastoma, anaplastic astrocytoma, oligoastrocytoma, oligodendroglioma), esophageal cancer, gastric cancer, gastrointestinal cancer, liver cancer, hepatocellular carcinoma (HCC) including childhood HCC, head and neck cancer (including head and neck squamous-cell carcinoma, nasopharyngeal carcinoma), Hurthle cell carcinoma, epithelial cancer, skin cancer, melanoma (including malignant melanoma), mesothelioma, lymphoma, myeloma (including multiple myeloma), leukemias, lung cancer (including non-small cell lung cancer (including all histological subtypes: adenocarcinoma, squamous cell carcinoma, bronchoalveolar carcinoma, large-cell carcinoma, and adenosquamous mixed type), small-cell lung cancer), ovarian cancer, pancreatic cancer, prostate cancer, kidney cancer (including but not limited to papillary renal cell carcinoma), intestine cancer, renal cell cancer (including hereditary and sporadic papillary renal cell cancer, Type I and Type II, and clear cell renal cell cancer); sarcomas, in particular osteosarcomas, clear cell sarcomas, and soft tissue sarcomas (including alveolar and (e.g. embryonal) rhabdomyosarcomas, alveolar soft part sarcomas); thyroid carcinoma (papillary and other subtypes).

MET inhibitors are e.g. also useful in the treatment of cancer wherein the cancer is stomach, colon, liver, genital, urinary, melanoma, or prostate. In a particular embodiment, the cancer is liver or esophageal.

MET inhibitors are e.g. also useful in the treatment of colon cancer, including metastases, e.g. in the liver, and of non-small-cell lung carcinoma.

MET inhibitors are e.g. also may be used in the treatment of hereditary papillary renal carcinoma (Schmidt, L. et al. Nat. Genet. 16, 68-73, 1997) and other proliferative diseases in which c-MET is overexpressed or constitutively activated by mutations (Jeffers and Vande Woude. Oncogene 18, 5120-5125, 1999; and reference cited therein) or chromosomal rearrangements (e.g. TPR-MET; Cooper et al. Nature 311, 29-33, 1984; Park, et al. Cell 45, 895-904, 1986).

MET inhibitors are e.g. further useful in the treatment of additional cancers and conditions as provided herein or known in the art.

MET inhibitors are e.g. also suitable for the treatment of one or more inflammatory conditions.

In a further embodiment, the inflammatory condition is due to an infection. In one embodiment, the method of treatment would be to block pathogen infection. In a particular embodiment, the infection is a bacterial infection, e.g., a *Listeria* infection. See, e.g., Shen et al. Cell 103: 501-10, (2000) whereby a bacterial surface protein activates c-Met kinase through binding to the extracellular domain of the receptor, thereby mimicking the effect of the cognate ligand HGF/SF.

The combination product of the present invention is especially appropriate for treatment of any of the cancers mentioned above amenable to EGFR or Met inhibitor treatment, especially a cancer selected from adenocarcinoma (especially of the breast or more especially of the lung), rhabdomyosarcoma, osteosarcoma, urinary bladder carcinoma, colorectal cancer and glioma.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by cMet (MET) and/or mediated by EGFR activity, or (ii) characterized by activity (normal or abnormal) of cMet and/or of EGFR; or (2) reducing or inhibiting the activity of cMet and/or of EGFR; or (3) reducing or inhibiting the expression of cMet and/or EGFR. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of cMet and/or EGFR; or at least partially reducing or inhibiting the expression of MET and/or EGFR.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

"And/or" means that each one or both or all of the components or features of a list are possible variants, especially two or more thereof in an alternative or cumulative way.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The term "treatment" comprises, for example, the prophylactic or especially therapeutic administration of the combination partners to a warm-blooded animal, preferably to a human being, in need of such treatment with the aim to cure the disease or to have an effect on disease regression or on the delay of progression of a disease.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

The combinations according to the invention can be prepared in a manner known per se and are those suitable for enteral, such as oral or rectal, and parenteral administration to mammals (warm-blooded animals), including man, comprising a therapeutically effective amount of at least one pharmacologically active combination partner alone or in combination with one or more pharmaceutically acceptable carriers, especially suitable for enteral or parenteral application. In one embodiment of the invention, one or more of the active ingredients are administered orally.

As used herein, the term "carrier" or "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The pharmaceutical combination product according to the invention (as fixed combination, or as kit, e.g. as combination of a fixed combination and individual formulations for one or both combination partners oras kit of individual formulations of the combination partners) comprises the combination partners (at least one MET tyrosine kinase inhibitor, at least one EGFR tyrosine kinase inhibitor, and optionally one or more further co-agents) of the present invention and one or more pharmaceutically acceptable carrier materials (carriers, excipients). The combination products or the combination partners constituting it can be formulated for particular routes of administration such as oral administration, parenteral administration, and rectal administration, etc. In addition, the combination products of the present invention can be made up in a solid form (including without limitation capsules, tablets, pills, granules, powders or suppositories), or in a liquid form (including without limitation solutions, suspensions or emulsions). The combination products and/or their combination partners can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

In one embodiment, the pharmaceutical compositions are tablets or gelatin capsules comprising the active ingredient together with one or more commonly known carriers, e.g. one or more carriers selected from the group consisting of a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

Tablets may be either film coated or enteric coated according to methods known in the art.

Suitable compositions for oral administration especially include an effective amount of one or more or in case of fixed combination formulations each of the combination partners (active ingredients) in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient(s) in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions (especially useful e.g. where antibodies are used as EGFR inhibitors) are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of one or more active ingredients with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention relates also to a kit of parts or a fixed pharmaceutical composition comprising an effective amount, especially an amount effective in the treatment of one of the above-mentioned diseases of at least one MET tyrosine kinase inhibitor, at least one EGFR tyrosine kinase inhibitor, or a pharmaceutically acceptable salt thereof, respectively, and optionally of at least one further co-agent, or a pharmaceutically acceptable salt thereof, together with one or more pharmaceutically acceptable carriers that are suitable for topical, enteral, for example oral or rectal, or parenteral administration and that may be inorganic or organic, solid or liquid.

In all formulations, the active ingredient(s) forming part of a combination product according to the present invention can be present each in a relative amount of 0.5 to 95% of weight of the corresponding formulation (regarding the formulation as such, that is without packaging and leaflet), e.g. from 1 to 90, 5 to 95, 10 to 98 or 10 to 60 or 40 to 80% by weight, respectively.

The dosage of the active ingredient to be applied to a warm-blooded animal depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. The dose of each of the combination partners or a pharmaceutically acceptable salt thereof to be administered to warm-blooded animals, for example humans of approximately 70 kg body weight, is preferably from approximately 3 mg to approximately 5 g, more preferably from approximately 10 mg to approximately 1.5 g per person per day, e.g. divided preferably into 1 to 3 single doses, e.g. for use once or twice daily, which may, for example, be of the same size. Usually, children receive half of the adult dose.

The pharmaceutical combination product of the present invention can e.g. be in unit dosage of about 1-1000 mg of active ingredient(s) for a subject of about 50-70 kg, or about 1-500 mg or about 1-250 mg or about 1-150 mg or about 0.5-100 mg, or about 1-50 mg of for any one or in particular the sum of active ingredients; or (especially for the EGFR inhibitor) 50 to 900, 60 to 850, 75 to 800 or 100 to 600 mg, respectively, for any one or in particular the sum of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or (in animal use) veterinarian of ordinary skill can readily determine the effective amount of each of the active ingredients necessary to prevent, treat or inhibit the progress of the disorder or disease.

Specific embodiments of the invention are also given in the claims which are incorporated here by reference, as well as in the Examples.

Female athymic mice bearing HCC827GR5 subcutaneous xenografts were treated with 2-fluoro-N-methyl-4-[(7-quinolin-6-yl-methyl)-imidazo[1,2-b]triazin-2-yl]benzamide, gefitinib, a combination of both agents or vehicle control at the indicated doses and schedules. Treatments started 11 days post tumor cells implantation and lasted 13 consecutive days. At the end of the second efficacy experiment (day 24 post cell injection), the groups treated with 2-fluoro-N-methyl-4-[(7-quinolin-6-yl-methyl)-imidazo[1,2-b]triazin-2-yl]benzamide and the combination group were split into two groups of four animals each. Four animals were kept under observation, without any treatment (left panel) while the two other groups of 4 animals each were kept under daily treatment as before (right panel). Tumor volumes and body weights were recorded only once a week. Horizontal lines are set at 100 and 500 mm$^3$ tumor volumes.

EXAMPLES

The following Examples illustrate the invention and provide specific embodiments, however without limiting the scope of the invention.
Abbreviations of Companies and Cell Depositories
ATCC=American Type Culture Collection, Manassas, Va., USA
Amimed=trademark of BioConcept, Allschwil, Switzerland
Applied Biosystems=Applied Biosystems, Foster City, Calif., USA
Gibco=belonging to Life Technologies Corporation, Grand Island, N.Y., USA
Pepro Tech=PeproTech, Rocky Hill, N.J., USA
Quiagen=Quiagen AG, Hilden, Germany
TPP=Techno Plastic Products AG, Trasadingen, Switzerland
Other Abbreviations:
DMSO=dimethyl sulfoxide Example 1: In-Vitro Combination of the MET Inhibitor 2-fluoro-N-methyl-4-[(7-quinolin-6-ylmethyl)-imidazo[1,2-b]triazin-2-yl]benzamide and the EGFR Inhibitor Gefitinib in a Lung Cancer Model In order to confirm the rationale of combined treatment, a combination of the title compounds was tested in the lung cancer cell line HCC827 and its gefinitib-resistant derivative, HCC827 GR. It could be shown that the combination of the MET inhibitor and the EGFR inhibitor was more effective as follows:
Methods:
HCC827 GR (gefitinib resistant) were obtained from Dr. Pasi A. Jänne (Dana-Farber Cancer Institute, Boston, Mass., USA), see also J. A. Engelman et al., Science 316, 1039 ff (2007). Cell line identity has been confirmed by SNP genotyping. Parental HCC827 cells are commercially available from ATCC (ATCC Number CRL-2868). All two NSCLC lines were grown in RPMI 1640 medium (Amimed, catalogue number 1-41F01-I) supplemented with 10% heat inactivated FCS, (Amimed, catalogue number 2-01F16-I), 2 mM L-glutamine (Amimed, catalogue number 5-10K00-H), 1 mM sodium pyruvate (Amimed, catalogue number 5-60F00-H) and 10 mM HEPES (Gibco, catalogue number 15630). Cells were incubated at 37° C. in a humidified atmosphere with 5% CO$_2$. DNA was extracted with a DNeasy Blood and Tissue Kit (QIAGEN, Inc).
The MET inhibitor and gefitinib 10 mM stock solutions were prepared in DMSO and stored at −20° C.

Figure 1:
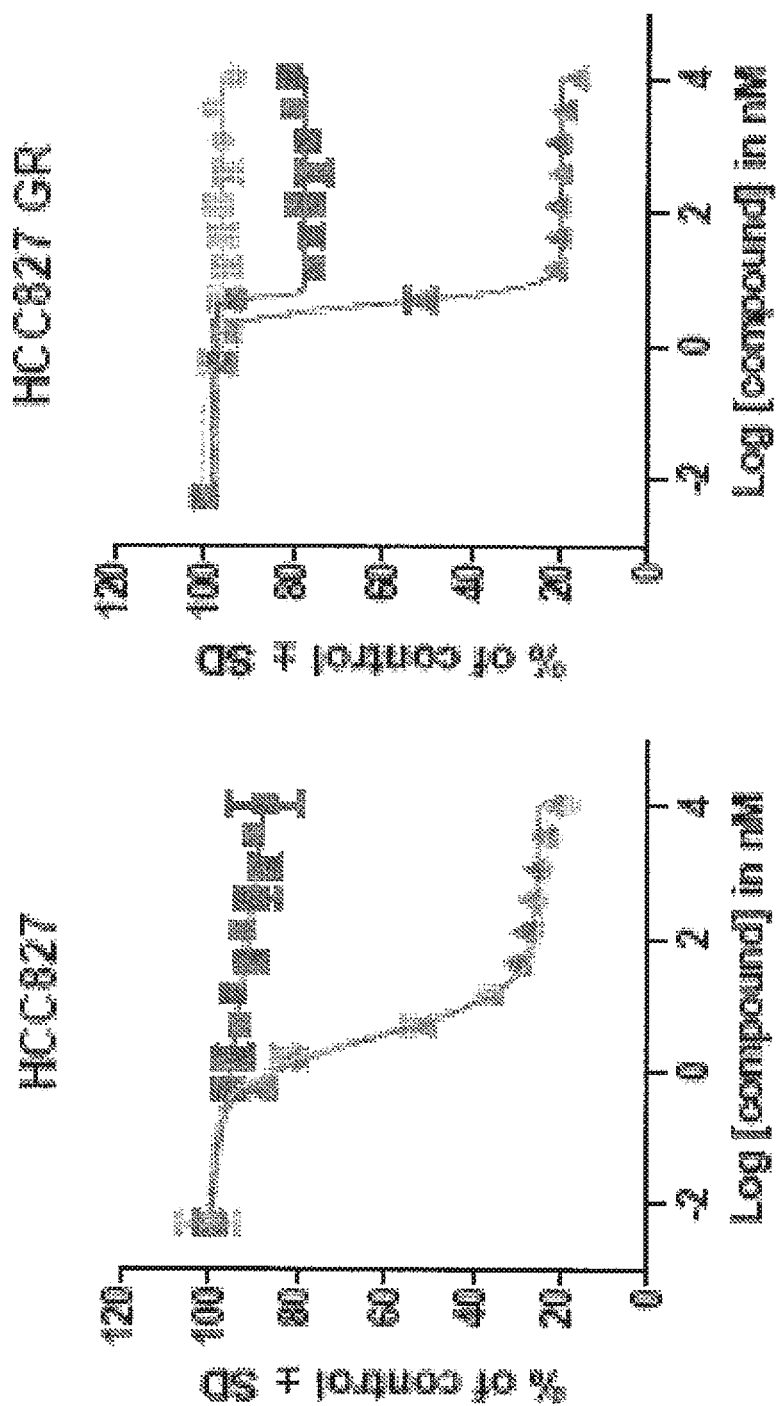
FIG. 1: Graphic representation of the in vitro effect of a combination of the MET inhibitor 2-fluoro-N-methyl-4-[(7-quinolin-6-yl-methyl)-imidazo[1,2-b]triazin-2-yl]benzamide and the EGFR inhibitor gefitinib which overcomes resistance to single agent gefitinib in HCC827 GR lung cancer cells; round spots: gefitinib; squares: 2-fluoro-N-methyl-4-[(7-quinolin-6-yl-methyl)-imidazo[1,2-b]triazin-2-yl]benzamide; triangles: gefitinib and 2-fluoro-N-methyl-4-[(7-quinolin-6-yl-methyl)-imidazo[1,2-b]triazin-2-yl] benzamide combination.

Proliferation Assays
Cells were seeded at 3000 per well in 96-well-plates (TPP, flat bottom, tissue culture-treated, product #92096). 24 h later, a 10-point dilution series of each compound was prepared in DMSO. For gefitinib: 3-fold steps, ranging from 10 mM to 0.5 µM; for 2-fluoro-N-methyl-4-[(7-quinolin-6-yl-methyl)-imidazo[1,2-b]triazin-2-yl]benzamide: 3-fold steps, ranging from 1 µM to 0.05 µM. Compounds were then diluted 1000-fold in growth medium in two steps and added to cells in triplicates, resulting in a final volume of 100 µL per well and maximal final compound concentrations of 10 µM for gefitinib and 1 µM for 2-fluoro-N-methyl-4-[(7-quinolin-6-yl-methyl)-imidazo[1,2-b]triazin-2-yl]benzamide. A DMSO-only control was included. For combination treatment, the gefitinib and 2-fluoro-N-methyl-4-[(7-quinolin-6-yl-methyl)-imidazo[1,2-b]triazin-2-yl] benzamide dilution series were added to cells simultaneously, i.e. compounds were mixed at a constant ratio of 10:1. Recombinant human HGF (PeproTech, catalogue number 100-39) was added together with compounds at a constant concentration as indicated in the respective experiments. Cells were incubated for 72 to 96 h and the amount of viable cells was then assessed using a resazurin sodium salt dye reduction readout (commercially known as AlamarBlue® assay, Invitrogen, Life Technologies Corporation, Grand Island, N.Y., USA). Values were normalized and plotted as either "% of control" with the DMSO control set to 100%, or as "fold seeded cells". In this case a resazurin readout of separate wells with untreated cells was obtained 24 h after seeding in order to determine a "seeded cells" value for normalization. Plotting of the data and curve-fitting were done with GraphPad Prism version 5.00 for Windows (GraphPad Software, Inc., La Jolla, Calif., USA).
Results:
FIG. 1 shows the results of the experiments. The HCC827 cells were, as expected, highly sensitive to gefinitib with an IC$_{50}$ of 3 to 4 nM. 2-fluoro-N-methyl-4-[(7-quinolin-6-yl-methyl)-imidazo[1,2-b]triazin-2-yl]benzamide did not show any substantial effect on proliferation of the HCC827 cells or any contribution to the effect of the gefitinib/2-fluoro-N-methyl-4-[(7-quinolin-6-yl-methyl)-imidazo[1,2-b]triazin-2-yl]benzamide combination. In clear contrast, HCC827 GR cells were fully resistant to gefitinib alone, and the effect of 2-fluoro-N-methyl-4-[(7-quinolin-6-ylmethyl)-imidazo[1,2-b]triazin-2-yl]benzamide monotherapy was modest. However, the combination of both agents inhibited proliferation as efficiently as gefinitib inhibited parental (not GR) cells, with an IC$_{50}$ of around 4 nM gefitinib and 0.4 nM 2-fluoro-N-methyl-4-[(7-quinolin-6-ylmethyl)-imidazo[1,2-b]triazin-2-yl]benzamide in a 10:1 mixture.

Figure 2:
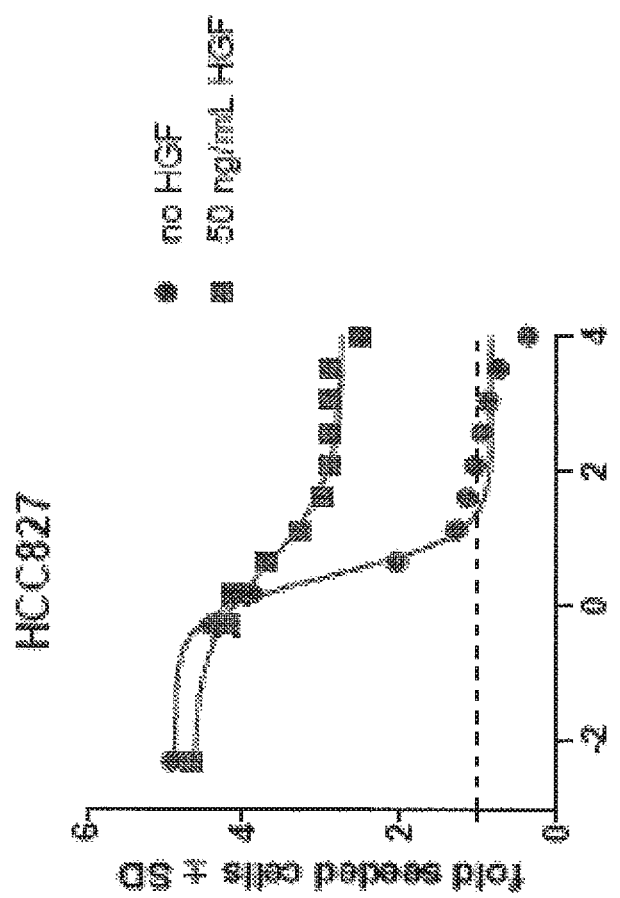
FIG. 2: Graphic representation of the in vitro effect of exogenous HGF (hepatocyte growth factor) which renders HCC827 cells resistant to gefitinib.

Example 2: Exogenous HGF as an Alternative Way of MET Activation Causes Resistance of HCC827 Cells to Gefitinib Experimental:
HCC827 cells were treated with a dilution series of gefitinib in the presence or absence of 50 ng/ml recombinant HGF (PeproTech, catalogue number 100-39) Cell viability was measured after 96 hours using an AlamarBlue assay. The initial amount of cells was quantified at the time of compound addition (dashed line), and cell growth on the y axis is expressed as a multiple of this value.
Results:
Growth of HCC827 cells exposed to a serial dilution of gefitinib in the presence or absence of a fixed combination of recombinant hepatocyte growth factor (HGF) was examined. As shown in FIG. 2, for the gefitinib-sensitive lung cancer cell line HCC827 HGF-mediated MET activation could partially revert growth inhibition caused by gefitinib, confirming the concept that MET activity can compensate for loss of EGFR activity in lung cancer models. Addition of MET inhibitor 2-fluoro-N-methyl-4-[(7-quinolin-6-yl-methyl)-imidazo[1,2-b]triazin-2-yl]benzamide would then be expected to revert the "rescue" of growth of the cells caused by HGF.

By quantitative Gene copy number analysis using qPCT (not shown) it was found that the average MET copy number in HCC827 GR and HCC827 cells were 7.50±0.18 and 1.92±0.36, respectively, thus confirming the concept that the acquired resistance of HCC827 GR to the EGFR inhibitor gefitinib is based on MET amplification.

Example 3: In-Vivo Combination of the MET Inhibitor 2-fluoro-N-methyl-4-[(7-quinolin-6-yl-methyl)-imidazo[1,2-b]triazin-2-yl]benzamide and the EGFR Inhibitor Gefitinib in a Lung Cancer Model 2-Fluoro-N-methyl-4-[(7-quinolin-6-yl-methyl)-imidazo[1,2-b]triazin-2-yl]benzamide was tested against HCC827 GR5 subcutaneous xenografts, either alone or in combination with gefitinib. This tumor model harbors an activating EGFR mutation as well as amplification of the MET gene.

Experiments were conducted under approval by the Basel Cantonal Veterinary Office.

Experiments were performed in female Hsd: Athymic nude-nu CPB mice obtained from Harlan Winkelmann, Germany. Animally were approximately 11 weeks of age at treatment start and housed under Optimized Hygienic Conditions (OHC) in Macrolon type III cages (max. 5 animals per cage) with free access to food and water.

HCC827GR5 (see also J. A. Engelman et al., Science 316, 1039 ff (2007); gefitinib resistant lung tumor cells) were obtained from Dr. Pasi Jänne (Dana-Farber Cancer Institute, Boston, Mass., USA). Cell line identity has been confirmed by SNP genotyping. Cells were grown in RPMI 1640 medium (Amimed #1-41F01-1) supplemented with 10% heat inactivated FCS, (Amimed #2-01F16-1), 2 mM L-glutamine (Amimed #5-10K00-H), 1 mM sodium pyruvate (Amimed #5-60F00-H) and 10 mM HEPES (Gibco #15630). Selective pressure was maintained on the cells by keeping a 0.1 µM gefitinib concentration in the cell culture medium at all times. Cells were incubated at 37° C. in a humidified atmosphere with 5% CO.

HCC827GR5 tumors were established by subcutaneous injection of 5×106 cells in 115 µl HBSS (Hank's buffered salt solution) containing 50% Matrigel (v/v) (gelatinous protein mixture secreted by Engelbreth-Holm-Swarm (EHS) mouse sarcoma cells, BD Biosciences, Franklin Lakes, N.J., USA) into the right flank of mice, with a 13 gauge trocar needle under Forene® (Isofluran; Abott, Switzerland) anesthesia. In the efficacy experiments, treatments started when the tumors reached an average size of 150 mm$^3$, 11 days post tumor implantation. In the PK/PD experiment, treatments were started when the mean tumor size was 450 mm$^3$, 15 days post tumor implantation.

2-Fluoro-N-methyl-4-[(7-quinolin-6-yl-methyl)-imidazo[1,2-b]triazin-2-yl]benzamide was formulated in 0.25% methylcellulose and 0.05% Tween 80 in water, using a water bath sonicator (33 kHz, 1 hour). The application volumes were 10 ml/kg for the single agents and for the vehicle control group or 5 ml/kg when the test compounds were given in combination. All indicated doses refer to free base equivalent of 2-Fluoro-N-methyl-4-[(7-quinolin-6-yl-methyl)-imidazo[1,2-b]triazin-2-yl]benzamide (dihydrochloride salt). Gefitinib was formulated in N-methyl-2-pyrrolidone:PEG300:Solutol HS15:water (10:30:20:40 v/v). (Trademarks: Tween 80=Polysorbat 80 (ICI Americas, Inc., USA); Solutol HS15=Macrogol 15 Hydroxystearate (BASF, Ludwigshafen, Germany)).

Tumor volumes were measured with calipers and determined according to the formula length×diameter$^2$×π/6. In addition to presenting changed of tumor volumes over the course of treatments, antitumor activity is expressed as T/C % ((mean change of tumor volume of treated animals/mean change of tumor volume of control animals)×100). Regressions (%) were calculated according to the formula ((mean tumor volume at end of treatment−mean tumor volume at start of treatment)/mean tumor volume at start of treatment)×100. Body weights and tumor volumes were recorded twice a week.

Statistics: Were applicable, data is presented as mean±SEM. For all tests, the level of significance was set at $p<0.05$. For tumor volumes, comparisons between treatment groups and vehicle control group were done using one-way ANOVA followed by Dunnett's test. Pairwise comparisons were done using a one way ANOVA followed by Tukey's test. The level of significance of body weight change within a group between the start and the end of the treatment period was determined using a paired t-test. Comparisons of delta body weighs between treatment and vehicle control groups were performed by a one-way ANOVA followed by a post hoc Dunnett's test. Calculations were performed using GraphPad Prism 4 for Windows (GraphPad Software Inc.). In addition, an approximation of drug interactions was made using the method described by Clarke (Clarke R., Breast Cancer Research and Treatment 46, 255-278 (1997)). This was applied to delta tumor volumes and can estimate interactions from limited data. In short, the combination data was assessed using the method presented by Clarke which can estimate interactions from limited data. For compound A, B or the combination AB (with control group C), antagonism is predicted when the calculation AB/C>A/C×B/C, additive effect: AB/C=A/C×B/C, synergistic interactions are predicted to occur when AB/C<A/C×B/C.

Figure 3:
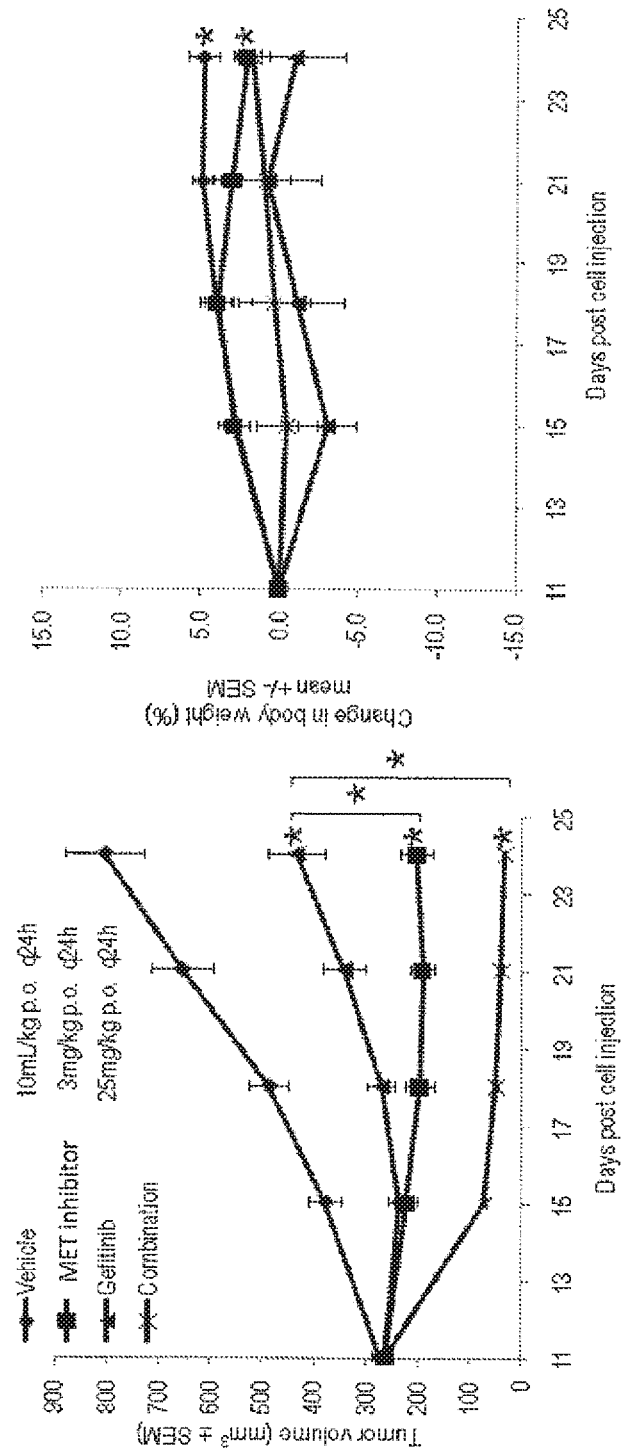
FIG. 3: Graphic representation of the first combination experiment of the MET inhibitor 2-fluoro-N-methyl-4-[(7-quinolin-6-yl-methyl)-imidazo[1,2-b]triazin-2-yl]benzamide and the EGFR inhibitor gefitinib in mice (in vivo) given in the Examples. Female athymic mice bearing HCC827GR5 subcutaneous xenografts were treated with 2-fluoro-N-methyl-4-[(7-quinolin-6-yl-methyl)-imidazo[1,2-b]triazin-2-yl]benzamide, gefitinib, a combination of both agents or vehicle control at the indicated doses and schedules. Treatments started 11 days post tumor cells implantation and lasted 13 consecutive days. Statistics on Δ tumor volumes and Δ body weights were performed with a one-way ANOVA, post hoc Dunnett's (*$p<0.05$ vs. vehicle controls) to compare treatment groups against the vehicle control group, and a one-way ANOVA, post hoc Tukey's fort pair-wise comparisons (*$p<0.05$ between linked groups). Left side: Tumor volumes over time. Right graph: Body weights over time.

In one experiment, see FIG. 3, female athymic nude mice were treated orally once a day with 3 mg/kg 2-fluoro-N-methyl-4-[(7-quinolin-6-yl-methyl)-imidazo[1,2-b]triazin-2-yl]benzamide, alone or in combination with 25 mg/kg gefitinib. Vehicle controls consisted of animals receiving a daily oral administration of 0.25% methylcellulose and 0.05% Tween 80 in water. All administration volumes were 10 ml/kg except in the combination chemotherapy group, where each single agent was administered at 5 ml/kg. When administered as single agents, both 2-fluoro-N-methyl-4-[(7-quinolin-6-yl-methyl)-imidazo[1,2-b]triazin-2-yl]benzamide and gefitinib produced a statistically significant antitumor effect (p<0.05, ANOVA), with 22.9% regressions and a T/C of 32.5%, respectively. When given in combination, 2-fluoro-N-methyl-4-[(7-quinolin-6-yl-methyl)-imidazo[1, 2-b]triazin-2-yl]benzamide and gefitinib produced statistically significant regressions of 87.3% (p<0.05, ANOVA). A post hoc Tukey'a analysis also showed that the antitumor effects produced by gefitinib administered as a single agent was statistically different from both 2-fluoro-N-methyl-4-[(7-quinolin-6-yl-methyl)-imidazo[1,2-b]triazin-2-yl]benzamide alone and in combination (p<0.05, ANOVA). In addition, 2-fluoro-N-methyl-4-[(7-quinolin-6-yl-methyl)-imidazo[1,2-b]triazin-2-yl]benzamide administered as a single agent did not produce a significant effect when compared to the combination (p>0.05, ANOVA, post hoc Tukey's). The body weight changes in all treatment groups were not significantly different from the vehicle control group (p>0.05, one way ANOVA, post hoc Dunnett's), and the body weight increase during the treatment period was significant only in the vehicle control group (p<0.05, paired t-test). Moreover, an analysis of possible compound interactions with the method described by Clarke (loc. cit.) indicated a synergistic antitumor effect with the combination of 2-fluoro-N-methyl-4-[(7-quinolin-6-yl-methyl)-imidazo[1,2-b]triazin-2-yl]benzamide (3 mg/kg) and gefitinib (25 mg/kg), see Table 1:

TABLE 1

Evaluation of the antitumor effect of the combination of 2-fluoro-N-methyl-4-[(7-quinolin-6-yl-methyl)-imidazo[1,2-b]triazin-2-yl]benzamide ("MET inhibitor") and gefitinib ("EGFR inhibitor") by Clarke's method:

|  | C | A (MET inhibitor) | B (EGFR inhibitor) | AB (combination) | A/C | B/C | A/C × B/C | AB/C | Difference | Result |
|---|---|---|---|---|---|---|---|---|---|---|
| Delta tumor volume | 532 | −60.2 | 173.1 | −228.4 | −0.113 | 0.325 | −0.037 | −0.429 | −0.39 | Synergy |

The combination data was assessed using the method presented by Clarke which can estimate interactions from limited data. For compound A, B or the combination AB (with control groups C), antagonism is predicted when the calculation AB/C>A/C×B/C, additive effect: AB/C=A/C×B/C, synergistic interactions are predicted to occur when AB/C<A/C×B/C.

Figure 4:
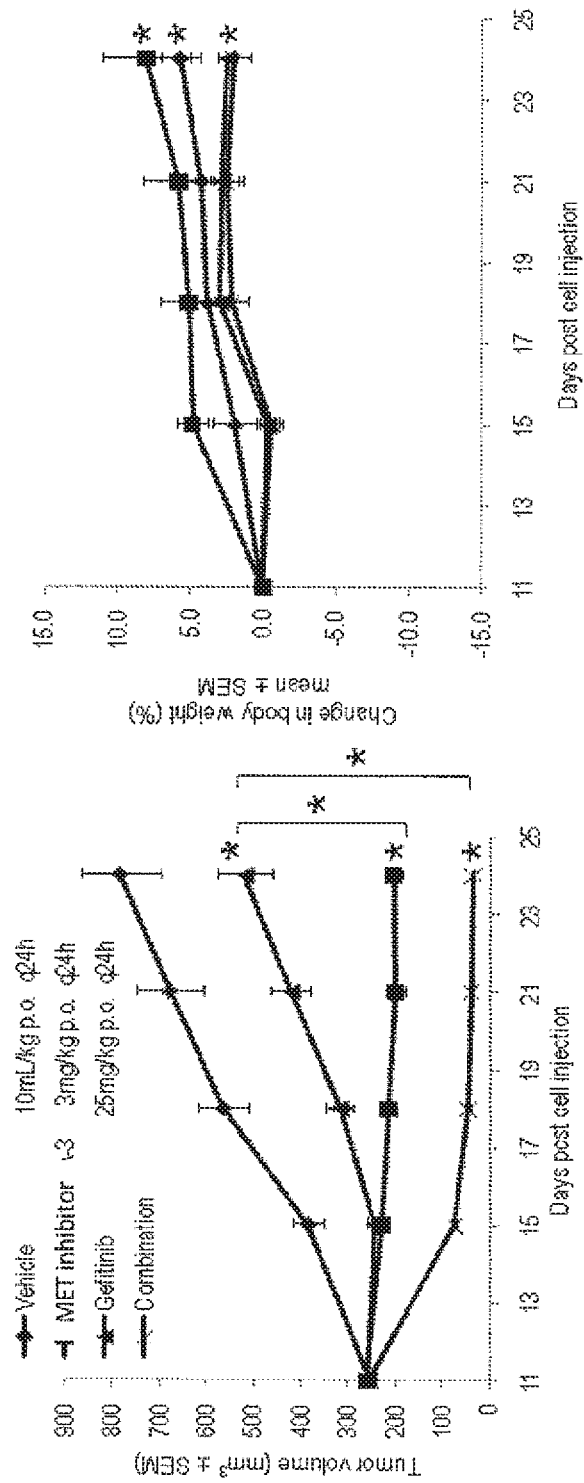
FIG. 4: Graphic representation of the second combination experiment of the MET inhibitor 2-fluoro-N-methyl-4-[(7-quinolin-6-yl-methyl)-imidazo[1,2-b]triazin-2-yl]benzamide and the EGFR inhibitor gefitinib in mice (in vivo) given in the Examples. Female athymic mice bearing HCC827GR5 subcutaneous xenografts were treated with 2-fluoro-N-methyl-4-[(7-quinolin-6-ylmethyl)-imidazo[1,2-b]triazin-2-yl]benzamide, gefitinib, a combination of both agents or vehicle control at the indicated doses and schedules. Treatments started 11 days post tumor cells implantation and lasted 13 consecutive days. Statistics on Δ tumor volumes and Δ body weights were performed with a one-way ANOVA, post hoc Dunnett's (*$p<0.05$ vs. vehicle controls) to compare groups versus vehicle, and a one-way ANOVA, post hoc Tukey's fort pair-wise comparisons (*$p<0.05$ between linked groups).

In a further experiment, see FIG. 4, female athymic nude mice were treated orally once a day with 3 mg/kg 2-fluoro-N-methyl-4-[(7-quinolin-6-yl-methyl)-imidazo[1,2-b]triazin-2-yl]benzamide, alone or in combination with 25 mg/kg gefitinib. Vehicle controls consisted of animals receiving a daily oral administration of 0.25% methylcellulose and 0.05% Tween 80 in water. All administration volumes were 10 ml/kg except in the combination chemotherapy group, where each single agent was administered at 5 ml/kg. When administered as single agents, both 2-fluoro-N-methyl-4-[(7-quinolin-6-yl-methyl)-imidazo[1,2-b]triazin-2-yl]benzamide and gefitinib produced a statistically significant antitumor effect (p<0.05, ANOVA), with 21.4% regressions and a T/C of 49.4%, respectively. When given in combination, 2-fluoro-N-methyl-4-[(7-quinolin-6-yl-methyl)-imidazo[1,2-b]triazin-2-yl]benzamide and gefitinib produced statistically significant regressions of 86.4% (p<0.05, ANOVA). A post hoc Tukey's analysis showed that the antitumor effects produced by gefitinib administered as a single agent was statistically different from both 2-fluoro-N-methyl-4-[(7-quinolin-6-yl-methyl)-imidazo[1,2-b]triazin-2-yl]benzamide alone and in combination (p<0.05, ANOVA). In addition, 2-fluoro-N-methyl-4-[(7-quinolin-6-yl-methyl)-imidazo[1,2-b]triazin-2-yl]benzamide administered as a single agent did not produce a significant effect when compared to the combination (p>0.05, ANOVA, post hoc Tukey's). The body weight changes in all treatment groups were not significantly different from the vehicle control group (p>0.05, one way ANOVA, post hoc Dunnett's). The body weight increase was statistically significant in all groups excepted the combination group (p<0.05, paired t-test). See FIG. 4.

As in the previous study, an analysis of possible compound interactions with the method described by Clarke (Clarke 1997) indicated a synergistic antitumor effect with the combination of 2-fluoro-N-methyl-4-[(7-quinolin-6-yl-methyl)-imidazo[1,2-b]triazin-2-yl]benzamide (3 mg/kg) and gefitinib (25 mg/kg), see Table 2:

TABLE 2

Evaluation of the antitumor effect of the combination of 2-fluoro-N-methyl-4-[(7-quinolin-6-yl-methyl)-imidazo[1,2-b]triazin-2-yl]benzamide ("MET inhibitor") and gefitinib ("EGFR inhibitor") by Clarke's method:

|  | C | A (MET inhibitor) | B (EGFR inhibitor) | AB (combination) | A/C | B/C | A/C × B/C | AB/C | Difference | Result |
|---|---|---|---|---|---|---|---|---|---|---|
| Delta tumor volume | 527.9 | −55.7 | 261 | −219.2 | −0.106 | 0.494 | −0.052 | −0.415 | −0.36 | Synergy |

(explanation see under Table 1)

Figure 5:
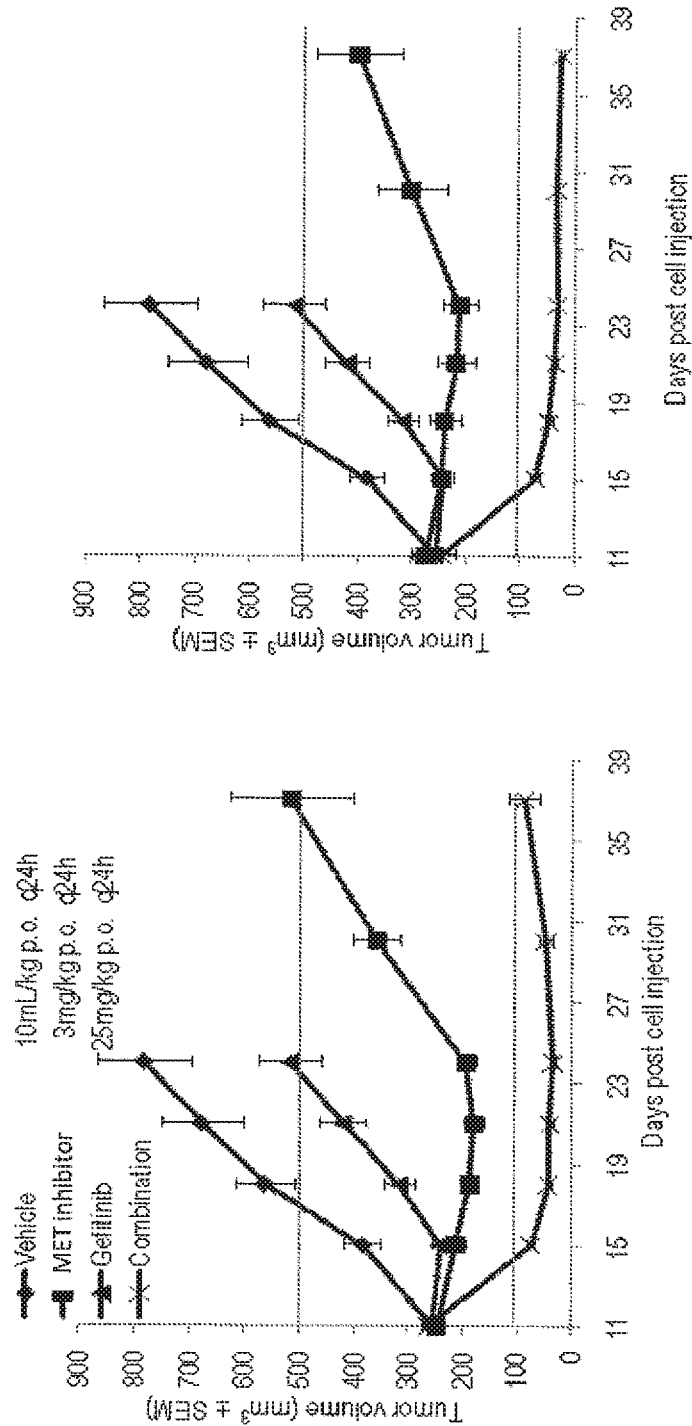
FIG. 5: Graphic representation of the change of tumor volumes over time after treatment discontinuation in mice (in vivo) as described in more detail in the Examples.

In a further experiment, female athymic mice bearing HCC827GR5 subcutaneous xenografts were treated with 2-fluoro-N-methyl-4-[(7-quinolin-6-yl-methyl)-imidazo[1,2-b]triazin-2-yl]benzamide, gefitinib, a combination of both agents or vehicle control at the doses and schedules indicated in FIG. 5. Treatments started 11 days post tumor cells implantation and lasted 13 consecutive days. At the end of the second efficacy experiment (day 24 post cell injection), the groups treated with 2-fluoro-N-methyl-4-[(7-quinolin-6-yl-methyl)-imidazo[1,2-b]triazin-2-yl]benzamide and the combination group were split into two groups of four animals each. Four animals were kept under observation, without any treatment (left panel) while the two other groups of 4 animals each were kept under daily treatment as before (right panel). Tumor volumes and body weights were recorded only once a week. Horizontal lines are set at 100 and 500 mm$^3$ tumor volumes, respectively. The tumors in the animals previously treated with 2-fluoro-N-methyl-4-[(7-quinolin-6-yl-methyl)-imidazo[1,2-b]triazin-2-yl]benzamide alone kept growing to a mean+/−SEM volume of 516+/−112 mm$^3$, while the tumors of the animals in the combination group reached 90+/−27 mm$^3$, see FIG. 5, left graph. In contrast, the animals in the groups where treatments were extended increased only to a mean of 400+/−80 mm$^3$ for the 2-fluoro-N-methyl-4-[(7-quinolin-6-yl-methyl)-imidazo[1,2-b]triazin-2-yl]benzamide-treated animals. The tumors in the animals that received the combination therapy continued to regress from a mean volume of 33+/−1.3 to 26.3+/−2.8 mm$^3$ (representing a mean of 89.2% regression from the initial volume).

Discussion: The MET inhibitor 2-fluoro-N-methyl-4-[(7-quinolin-6-yl-methyl)-imidazo[1,2-b]triazin-2-yl]benzamide at a dose of 3 mg/kg showed slight statistically significant tumor regressions. These regressions were significantly increased when 2-fluoro-N-methyl-4-[(7-quinolin-6-yl-methyl)-imidazo[1,2-b]triazin-2-yl]benzamide was combined with gefitinib. As a single agent, gefitinib administered at a dose of 25 mg/kg consistently caused statistically significant antitumor effects, but never regressions. Pharmacodynamic analysis showed that the MET signaling pathway was down regulated for at least 8 hours after administration of the MET inhibitor and that this down regulation was reinforced by the simultaneous administration of the EGFR inhibitor gefitinib, accounting for strong tumor regressions of more than 80% in the combination groups. The analysis of the drug concentrations after repeated dosing (not shown) showed that the levels of gefitinib were increased by 2- to 4-fold when it was administered in combination. Therefore it is possible that the incrased exposure to gefitinib in the tumor tissue contributes to the improved antitumor effects observed in the combination groups.

Example 4

2-Fluoro-N-methyl-4-[(7-quinolin-6-yl-methyl)-imidazo[1,2-b]triazin-2-yl]benzamide is an ATP-competitive and reversible small molecule inhibitor against the c-MET kinase that possesses a high potency (IC50=0.13±0.05 nM nin vitro kinase assay) and selectivity (with >10,000-fold selectivity over a panel of 56 other human kinases). Potent activity (IC50 values: 0.2-2 nM) has also been demonstrated in cell-based biochemical and functional assays that measure c-MET-mediated signal transduction, as well as c-MET-dependent cell proliferation, survival and migration. In c-MET-driven or HGF/c-MET-driven xenograft mouse tumor models, oral dosing of 2-fluoro-N-methyl-4-[(7-quinolin-6-yl-methyl)-imidazo[1,2-b]triazin-2-yl]benzamide demonstrated significant in vivo activity in blocking both c-MET phosphorylation and tumor growth. In addition, combination with the EGFR inhibitor Gefitinib was effective in vitro and in vivo in suppressing growth of a Gefitinib-resistant lung cancer model harboring a Gefitinib-sensitive EGFR mutation and c-MET amplification. Gene copy number variation and mRNA expression profiling of a large panel of cancer cell lines originating from various lineages suggested that c-MET amplification exists in several cancer types but is relatively more frequent in cancers of the lung, stomach, breast and ovary. HGF expression also displays lineage association and is more frequently detected in cancers of the blood, brain, soft tissue, lung and liver. Pharmacogenetic profiling of these cancer cell lines with a large panel of targeted agents indicates that c-MET amplification or simultaneous HGF and c-MET expression is highly predictive of response to c-MET inhibitors including 2-fluoro-N-methyl-4-[(7-quinolin-6-ylmethyl)-imidazo[1,2-b]triazin-2-yl]benzamide. Furthermore, among 484 classes of compounds classified by target, c-MET inhibitors are the most active class of compounds in inhibiting the growth of cell lines with c-MET amplification or simultaneous HGF and c-MET expression. Importantly, cell lines with simultaneous HGF and c-MET expression are also relatively resistant to EGFR inhibitors compared to cell lines with similar c-MET level that lack HGF expression.

Example 5: Clinical Trial for Non-Small Cell Lung Cercinoma (NSCLC)

A safety and efficacy study of 2-fluoro-N-methyl-4-[(7-quinolin-6-yl-methyl)-imidazo[1,2-b]triazin-2-yl]benzamide and gefitinib in patients with EGFR mutated, c-MET-amplified NSCLC who have progressed after EGFRi treatment is conducted. The trial is a Phase IB/II, open label, multicenter study of 2-fluoro-N-methyl-4-[(7-quinolin-6-yl-methyl)-imidazo[1,2-b]triazin-2-yl]benzamide administered orally in combination with gefitinib in adult patients with EGFR mutated, c-MET-amplified non-small cell lung cancer who have progressed after EGFR inhibitor treatment.

Inclusion Criteria are:
  Documented EGFR mutation-Documented c-MET amplification-Prior clinical benefit on EGFR inhibitors and then subsequent progression
  No starting of other treatment since progression on EGFR inhibitors
  ≥18 year old-Life expectancy of ≥3 months
  ECOG performance status ≤2
  Gender: Both; Minimum age 16 Years Exclusion Criteria:
  Unable to swallow tables once or twice daily
  Previous treatment with c-MET inhibitor
  Any unresolved toxicity form previous anticancer therapy greater than grade 1-History of cystic fibrosis
  History of acute or chronic pancreatitis
  Unable to undergo MRI or CT sans
  Known history of HIV
  Undergone a bone marrow or sold organ transplant
  Clinically significant wound or lung tumor lesions with increased likelihood of bleeding
  Pregnant or nursing Other protocol-defined inclusion/exclusion criteria may apply The following data are obtained:
Primary Outcome Measures

| Outcome Measure | TimeFrame | Description | Safety Type |
|---|---|---|---|
| 1) Phase Ib: Frequency and characteristics of dose limiting toxicities | first cycle of study treatment | cycle = 28 days | Yes |

Secondary Outcome Measures

| Outcome Measure | TimeFrame | Description | Safety Type |
|---|---|---|---|
| Overall survival (OS) | From date of treatment until last patient is off study treatment | OS is defined as the time from the date of treatment to the date of death from any cause. | No |
| Safety via monitoring the frequency, duration, and severity of AEs and SAEs, changes in physical examination, clinical | 30 days post study treatment | SAE collection ends 30 days after the last study related procedure. | Yes |

| Outcome Measure | TimeFrame | Description | Safety Type |
|---|---|---|---|
| laboratory parameters, vital signs and ECGs | | | |
| Inhibition of c-MET signaling by pre- and post- treatment immunohistochemistry of p-c-MET, | Day 15 of cycle 1 | cycle 1 = 28 days | No |
| Plasma concentration of 2-fluoro-N-methyl-4-[(7-quinolin-6-yl-methyl)-imidazo[1,2-b]triazin-2-yl]benzamide and gefitinib, PK parameters including but not limited to AUC, Cmax, Tmax, half-life, accumulation ratio. | Day 1 of cycle 4 | cycle 4 = 28 days | No |
| Progression free survival (PFS) | From date of treatment to the date of progression disease | PFS is defined as the time from the date of treatment to the date of event defined as the first documented progression per RECIST or death due to any cause. | No |

Example 6

A Phase IB/II, open label multicenter study of Compound A or Compound B adminstered orally in combination with gefitinib in adult patients with EGFR mutated, c-MET-amplified non-small cell lung cancer who have progressed after EGFR inhibitor treatment Protocol Summary:

| Protocol | |
|---|---|
| Title | a Phase Ib/II, open-label, dose escalation and multicenter study of Compound A or Compound B administered orally in combination with gefitinib in adult patients with EGFR mutated and c-MET amplified NSCLC who have progressed after EGFR inhibitor treatment |
| Brief title | Study of efficacy and safety Compound A or Compound B + gefitinib in patients with NSCLC who have progressed after EGFR inhibitor treatment |
| Sponsor and Clinical Phase | Novartis Phase Ib/II |
| Investigation type | Drug |
| Study type | Interventional |
| Purpose and rationale | This study is designed to explore if the combination of the c-MET inhibitor, Compound A or Compound B, and the EGFR inhibitor, gefitinib, will provide meaningful clinical benefit to patients whose tumors have aberrations in both c-MET and EGFR pathways. |
| Primary Objective(s) and | 1) Phase Ib: To estimate the MTD or RP2D of Compound A or Compound B in combination with gefitinib in NSCLC patients who have c-MET gene amplification<br>2) Phase II: To estimate overall clinical activity of Compound A or Compound B in combination with gefitinib in NSCLC patients with c-MET gene amplification |
| Secondary Objectives | 1) To determine safety and tolerability of Compound A or Compound B in combination with gefitinib |
| | 2) To estimate time dependent clinical activity of Compound A or Compound B in combination with gefitinib<br>3) To assess the pharmacodynamic effect of Compound A or Compound B in combination with gefitinib<br>4) To characterize the PK profile of Compound A or Compound B and gefitinib in NSCLC patient population and to assess potential drug interaction between Compound A or Compound B and gefitinib |
| Study design | Open label, single arm, with a Phase Ib Part and a Phase II Part |
| Population | Approximately 58 male or female, at least 18 years old patients with EGFR mutated and c-MET amplified NSCLC who have progressed after EGFR inhibitor treatment |
| Inclusion criteria | Confirmed c-MET pathway dysregulation<br>EGFR mutated NSCLC patient who have developed acquired resistance to EGFR inhibitor treatment<br>Measurable disease as determined by RECIST version 1.1<br>ECOG performance status ≤2 |
| Exclusion criteria | Previous treatment with a c-MET inhibitor or HGF-targeting therapy<br>Previous radiation therapy completed less than 4 weeks prior to dosing and, if present, any acute toxicity > grade 1<br>History of cystic fibrosis<br>History of acute or chronic pancreatitis, surgery of pancreas or any risk factors that may increase the risk of pancreatitis |
| Investigational and reference therapy | All patients will be treated with Compound A or Compound B and gefitinib administered orally, beginning on Cycle 1 Day 1. Each cycle will have 28 days. All patients will continue to receive study treatment until disease progression, intolerable toxicity, withdrawal of consent, or discontinuation of treatment for any other reason |
| Efficacy assessments | Tumor response assessment as per RECIST v1.1. |
| Safety assessments | Incidence, frequency, and category of DLT during the first cycle of Compound A or Compound B treatment (escalation phase) Frequency, duration, and severity of AEs, SAEs |
| Other assessments | Compound A or Compound B and gefitinib pharmacokinetics assessment in blood samples Biomarker assessments |
| Data analysis | Data will be summarized using descriptive statistics (continuous data) and/or contingency tables (categorical data) for demographic and baseline characteristics, efficacy measurements, safety measurements, and all relevant PK and PD measures.<br>The Bayesian logistic regression model with overdose control will be used to recommend the dose levels that will be used for dose cohorts that occur after the initial dose cohort. |
| Key words | Compound A or Compound B, gefitinib, NSCLC, acquired resistance criteria, c-MET dysregulation |

The invention claimed is:

1. A pharmaceutical combination comprising (i) a MET tyrosine kinase inhibitor, which is the compound of formula (I)

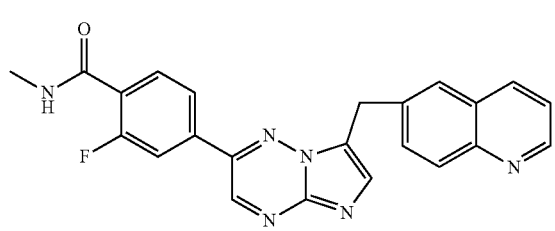

(I)

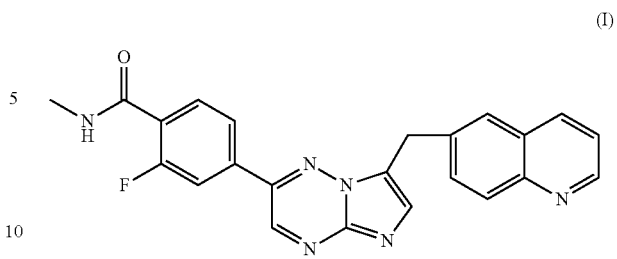

(I)

or a pharmaceutically acceptable salt thereof, and (ii) an EGFR tyrosine kinase inhibitor, which is gefitinib or a pharmaceutically acceptable salt thereof.

2. The pharmaceutical combination according to claim 1, for simultaneous, separate or sequential use of the components (i) and (ii).

3. The pharmaceutical combination according to claim 1, wherein the combination is in the form of a fixed combination.

4. The pharmaceutical combination according to claim 1, in the form of a kit of parts for the combined administration where the EGFR tyrosine kinase inhibitor and the MET tyrosine kinase inhibitor may be administered independently at the same time or separately within time intervals.

5. The pharmaceutical combination for according to claim 1, further comprising a co-agent, or a pharmaceutically acceptable salt thereof.

6. A pharmaceutical product or a commercial package comprising a combination or combination product according to claim 1, together with instructions for simultaneous, separate or sequential use thereof.

7. A method of treating an EGFR tyrosine kinase activity and/or MET tyrosine kinase activity mediated disease, which comprises simultaneous, separate or sequential administration to a subject in need of such treatment,
(i) a MET tyrosine kinase inhibitor which is 2-fluoro-N-methyl-4-[(7-quinolin-6-yl-methyl)-imidazo[1,2-b]triazin-2-yl]benzamide having the formula (I)

or a pharmaceutically acceptable salt or hydrate thereof, and (ii) an EGFR tyrosine kinase inhibitor which is gefitinib, or a pharmaceutically acceptable salt thereof, wherein treatment refers to ameliorating the disease or disorder, alleviating or ameliorating at least one physical parameter including those which may not be discernible by the patient, or modulating the disease or disorder, either physically, physiologically, or both.

8. The method of claim 7 wherein the EGFR tyrosine kinase activity and/or MET tyrosine kinase activity mediated disease is cancer.

9. The method according to claim 8, wherein the EGFR tyrosine kinase activity and MET tyrosine kinase activity mediated disease is a cancer selected from the group consisting of adenocarcinoma, rhabdomyosarcoma, osteosarcoma, urinary bladder carcinoma, colorectal cancer and glioma.

10. The method according to claim 7, wherein the EGFR tyrosine kinase activity and MET tyrosine kinase activity mediated disease is EGFR-mutated c-Met-amplified non-small cell lung cancer.

11. The method of claim 8, wherein the cancer is metastatic non-small cell lung cancer.

\* \* \* \* \*